(12) United States Patent
Kozhevnikov et al.

(10) Patent No.: US 9,461,255 B2
(45) Date of Patent: Oct. 4, 2016

(54) LIGHT EMITTING COMPOUNDS

(71) Applicant: University of Northumbria at Newcastle, Tyne and Wear (GB)

(72) Inventors: Valery Kozhevnikov, Tyne and Wear (GB); Pierre-Henri Lanoë, Tyne and Wear (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/420,207

(22) PCT Filed: Aug. 8, 2013

(86) PCT No.: PCT/GB2013/052128
§ 371 (c)(1),
(2) Date: Feb. 6, 2015

(87) PCT Pub. No.: WO2014/023972
PCT Pub. Date: Feb. 13, 2014

(65) Prior Publication Data
US 2015/0200369 A1  Jul. 16, 2015

(30) Foreign Application Priority Data

Aug. 9, 2012 (GB) .................. 1214258.4
May 24, 2013 (GB) .................. 1309420.6

(51) Int. Cl.
| | |
|---|---|
| C09K 11/06 | (2006.01) |
| C07F 15/00 | (2006.01) |
| C07D 239/24 | (2006.01) |
| H01L 51/00 | (2006.01) |
| H05B 33/14 | (2006.01) |
| H01L 51/50 | (2006.01) |

(52) U.S. Cl.
CPC ......... *H01L 51/009* (2013.01); *C07F 15/0033* (2013.01); *C07F 15/0086* (2013.01); *C09K 11/06* (2013.01); *H01L 51/0085* (2013.01); *H01L 51/0087* (2013.01); *H05B 33/14* (2013.01); *C09K 2211/1007* (2013.01); *C09K 2211/1029* (2013.01); *C09K 2211/1044* (2013.01); *C09K 2211/185* (2013.01); *H01L 51/5012* (2013.01); *H01L 51/5016* (2013.01)

(58) Field of Classification Search
CPC .............. C09K 11/06; H01L 51/5032; H01L 51/5004; H01L 51/0032; H01L 51/5296; H05B 33/14
USPC .......................................... 544/225
See application file for complete search history.

(56) References Cited

U.S. PATENT DOCUMENTS

| | | |
|---|---|---|
| 7,396,599 B2 | 7/2008 | Lyu et al. |
| 7,625,639 B2 | 12/2009 | Haga et al. |
| 2006/0115675 A1 | 6/2006 | Haga et al. |
| 2012/0199823 A1 | 8/2012 | Molt et al. |

FOREIGN PATENT DOCUMENTS

| | | |
|---|---|---|
| EP | 1961743 A1 | 8/2008 |
| JP | 2001060468 A | 3/2001 |
| KR | 2010-0084095 A | 7/2010 |

OTHER PUBLICATIONS

Credi et al., "Photophysical properties of a dinuclear rack-type Ru(II) complex and of its components", Chemical Physics Letters, vol. 243(1,2), 1995, pp. 102-107.
Ceroni et al., "Absorption and emission properties of di- and trinuclear ruthenium(II) rack-type complexes", European Journal of Inorganic Chemistry, vol. 9, 1999, pp. 1409-1414.
Heirtzler et al., "Dalton Transactions: Inorganic Chemistry", Journal of the Chemical Society, vol. 4, 1999, pp. 565-574.
Brown et al., "Di-[1,10]-phenanthrolinyl Diazines: A New Family of Bis-tridentate Chelators", Organic Letters, vol. 4(8), 2002, pp. 1253-1256.
Patroniak et al., "Luminescence properties of new complexes of Eu(III) and Tb(III) with heterotopic ligands", Spectrochimica Acta, Part A: Molecular and Biomolecular Spectroscopy, vol. 64A(4), 2006, pp. 830-834.
International Search Report dated Nov. 26, 2012 for Application No. GB1214258.4.
International Search Report dated Jun. 4, 2013 for Application No. GB1309420.6.
International Search Report for PCT/GB2013/052128 mailed Nov. 20, 2013.
International Written Opinion for PCT/GB2013/052128 mailed Nov. 20, 2013.

(Continued)

*Primary Examiner* — Venkataraman Balasubramanian
(74) *Attorney, Agent, or Firm* — Drinker Biddle & Reath LLP

(57) ABSTRACT

Claimed is a cyclometallated organometallic light emitting complex having two tridentate ligand portions sharing a central heterocycle "A" providing a binding-site for each of the two metals (formula I): Formula (I): A more illustrative embodiment is formula (XII): Characterizing for the invention is that either one of XI and X2 and either one of Y1 and Y2 is carbon. The dinuclear complexes are for use in OLEDs.

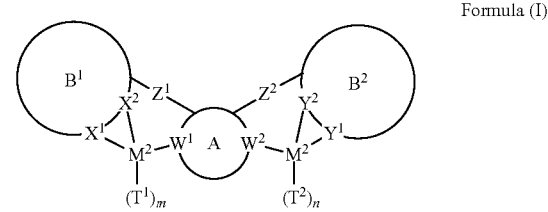

Formula (I)

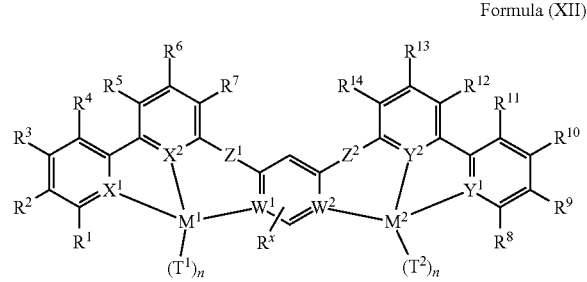

Formula (XII)

7 Claims, 3 Drawing Sheets

(56) References Cited

OTHER PUBLICATIONS

Auffrant et al., "Dinuclear Iridium(III) Complexes Consisting of Back-to-Back tpy-(ph)$_n$-tpy Bridging Ligands (n=0, 1 or 2) and Terminal Cyclometallating Tridentate N-C-N- Ligands", Inorganic Chemistry, vol. 45, No. 26, pp. 10990-10997, 2006.

Beley et al., "Pronounced Electronic Coupling in Rigidly Connected N,C,N-Coordinated Diruthenium Complexes over a Distance of Up to 20 Å", Communications, Angew. Chem. Int. Ed. Engl., 33, No. 17, pp. 1775-1778, 1994.

Hanan et al., "Coordination Arrays: Tetranuclear Cobalt (II) Complexes with [2x2]-Grid Structure", Communications, Angew. Chem. Int. Ed. Engl., 36, No. 17, pp. 1842-1844, 1997.

Hanan et al., "Synthesis, Structure, and Properties of Dinuclear and Trinuclear Rack-Type Ru$^{11}$ Complexes" Communciations, Angew, Chem, Int. Ed. Engl., 34, No. 10, pp. 1122-1124, 1995.

International Preliminary Report on Patentability from corresponding PCT application, PCT/GB2013/052128, Feb. 10, 2015.

Patoux et al., "Long-Range Electronic Coupling in Bis(cyclometalated) Ruthenium Complexes", J. Am. Chem. Soc., 120, pp. 3717-3725, 1998.

LIGHT EMITTING COMPOUNDS

CROSS-REFERENCE TO RELATED APPLICATIONS

This application is a national stage application (under 35 U.S.C. §371) of PCT/GB2013/052128, filed Aug. 8, 2013, which claims benefit of United Kingdom Application No. 1214258.4, filed Aug. 9, 2012, and United Kingdom Application No. 1309420.6, filed May 24, 2013, all of which are incorporated herein by reference in their entirety.

This invention relates to light emitting and phosphorescent compounds. Specifically, the invention relates to light emitting compounds with particular application in organic light emitting diodes.

BACKGROUND

Phosphoresecent organic light emitting diodes (OLEDs) have attracted considerable commercial and academic interest for application in high-quality, energy efficient flat-panel displays. Complexes based on cyclometallated second and third row transition metal centres (in particular iridium and platinum) exhibit highly efficient phosphorescence and have commonly been incorporated in these devices. OLEDs operate on the principle of electroluminescence. Typical OLEDs consist of several layers which are sandwiched between electrodes (Tang, et al., *Appl. Phys. Lett.* 1987, 51, 913). Upon applying an electric field, holes are injected from the anode and electrons are injected from the cathode of the OLED and migrate towards each other. When the charge carriers meet, they recombine with the emission of light of a certain wavelength according to the nature of the emitter used. The recombination process creates both singlet (25% probability) and triplet (75% probability) excitons. In simple organic molecules triplet excitons do not effectively produce emission of light and, therefore, the theoretical quantum efficiency is limited to approximately 25%. However, the introduction of metal centres like platinum and iridium, facilitates inter-system crossing between singlet and triplet states and promotes efficient radiative decay from triplet states to a ground state. Thus the use of cyclometallated second and third row transition metal centres in OLEDs allows the harvesting of both singlet and triplet type excitons therefore increasing the maximum obtainable internal quantum efficiency of the device. The introduction of two or more metal centres may further facilitate inter-system crossing between singlet and triplet states and thus may further increase efficiency.

In addition, complexes of this type are known to have further applications such as light emitting units of sensory molecular systems whose emission is modulated upon binding of a target analyte or as intrinsically emissive probes that may localize in selected organelles in living cells. Furthermore, they are under investigation as potential photocatalysts for "water splitting" to generate hydrogen, as sensitizers of energy and electron-transfer reactions and are also relevant to processes involving the conversion of solar energy to electrical energy. For these applications efficient absorption and emission in the red region of the electromagnetic spectrum is desired. Introducing a second metal centre is one way of shifting absorption and emission into the red without the need to extend the conjugation system of the ligand and potentially minimizes non-radiative decay pathways associated with band gap law which would lead to a decrease in quantum efficiency.

To date a variety of highly luminescent cyclometallated complexes with transition metal centres have been synthesized and many have been used in OLEDs and the other technological fields mentioned above. Typically such compounds contain a single metal centre surrounded by a number of ligands which bind to the metal via one or more donor atoms. Examples of cyclometallated complexes with one metal centre are disclosed in Brulatti et al., *Inorganic Chemistry*, 2012, 51(6), 3813-3826, wherein a series of monoiridium complexes based on tridentate NCN ligands are described. Luminescent cyclometallated complexes containing two metal centres have also been synthesized. Examples include bidentate ligands including di-iridium cyclometallated complexes (Tsuboyama et al., *Dalton Transactions*, 2004, (8), 1115-1116), platinum and iridium mixed metal complexes (Kozhevnikov et al., *Inorganic Chemistry*, 2011, 50(13), 6304-6313) and bimetallic complexes incorporating bidentate carbine ligands (Tennyson et al., *Inorganic Chemistry*, 2009, 48(14), 6924-6933). However, octahedral complexes formed from such ligands are often chiral and when two or more metal centres are present in one molecule complications can arise due to the formation of mixtures of diastereomers. As diastereomers have different chemical and physical properties characterisation of diastereomeric mixtures is very difficult and because the physical properties of the compounds contained therein are not uniform, application in OLEDs is compromised. To enhance the suitability of cyclometallated complexes for OLEDs it is therefore highly desirable that the diastereomers can be separated. Another approach is to use nonchiral metal centres. However, a very limited number of nonchiral multimetallic cyclometallated complexes have been investigated to date and none have demonstrated high luminescent yields for application to OLEDs. For example, di-ruthenium complexes coordinated by bis NCN cyclometallated ligands wherein the metal centres are connected by a flexible linker are known (Yang et al., *Organometallics* 2012). In addition, cyclometallated complexes with mixed metal centres held by cyclometallating terdentate ligands have been also synthesized (Wu et al., *Organometallics* 2012, 31(3), 1161-1167).

Despite the existence of multimetallic cyclometallated metal complexes, their full potential has yet to be realized. What is therefore needed are new highly luminescent multimetallic complexes which are easily synthesised and can deliver high luminescent quantum yields and be applied to OLEDs and other technology fields.

BRIEF SUMMARY OF THE DISCLOSURE

In accordance with the present invention there is provided a cyclometallated organometallic light emitting complex having a first tridentate ligand portion coordinated with a first metal and a second tridentate ligand portion coordinated with a second metal, the complex having a structure according to Formula (I):

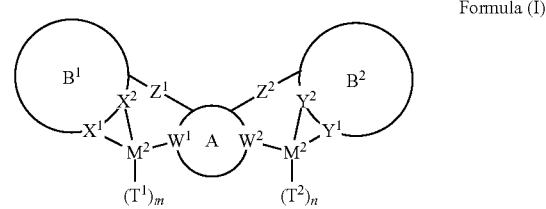

Formula (I)

wherein:

A is an aromatic heterocyclic moiety including coordinating heteroatoms $W^1$ and $W^2$;

$M^1$ and $M^2$ are metal atoms and may be the same or different;

$B^1$ is a ligand moiety including coordinating atoms $X^1$ and $X^2$ and $B^2$ is a ligand moiety including coordinating atoms $Y^1$ and $Y^2$, wherein $B^1$ and $B^2$ may be the same or different;

said first tridentate ligand portion includes atoms $X^1$, $X^2$ and $W^1$ coordinated to metal atom $M^1$;

said second tridentate ligand portion includes atoms $Y^1$, $Y^2$ and $W^2$ coordinated to metal atom $M^2$;

wherein at least one of atoms $X^1$, $X^2$ is connected to said metal atom $M^1$ via an organometallic bond and/or wherein at least one of atoms $Y^1$, $Y^2$ is connected to said metal atom $M^2$ via an organometallic bond;

$Z^1$ and $Z^2$ are one or more bonds or one or more connecting moieties by which $B^1$ and $B^2$ are respectively joined to A and $Z^1$ and $Z^2$ may be the same or different;

$T^1$ and $T^2$ are auxiliary ligands in which m and n are 0 or an integer sufficient to satisfy the respective coordination requirements of $M^1$ and $M^2$ and, where m and n are 2 or more, each respective auxiliary ligand may be the same or different.

Preferably, at least one of $X^1$, $X^2$, $Y^1$ and $Y^2$ is carbon.

Preferably, at least one of $X^1$ and $X^2$ is carbon and at least one of $Y^1$ and $Y^2$ is carbon.

Preferably, the complex of the invention is phosphorescent.

Preferably, $W^1$ and $W^2$ are each independently selected from the group consisting of nitrogen, sulphur and oxygen.

In much preferred embodiments, $W^1$ and $W^2$ are nitrogen.

Preferably, $M^1$ and $M^2$ are transition metals.

In preferred embodiments, $M^1$ and $M^2$ are each independently selected from the group consisting of iridium, palladium, osmium, rhenium, ruthenium, platinum and gold.

In further preferred embodiments, $M^1$ and $M^2$ are each independently selected from the group consisting of iridium, palladium, rhenium, platinum and gold.

In some preferred embodiments, $M^1$ and $M^2$ are each independently selected from iridium and platinum.

In some embodiments, $M^1$ and $M^2$ are iridium.

In other embodiments, one of $M^1$ and $M^2$ is iridium and the other of $M^1$ and $M^2$ is platinum.

Preferably in embodiments of the invention each of $X^1$, $X^2$, $Y^1$ and $Y^2$ is independently selected from carbon, nitrogen, sulphur and oxygen.

Particularly preferably in embodiments of the invention each of $X^1$, $X^2$, $Y^1$ and $Y^2$ is independently selected from carbon and nitrogen.

Preferably one of $X^1$ and $X^2$ is nitrogen and the other is carbon.

Preferably one of $Y^1$ and $Y^2$ is nitrogen and the other is carbon.

Preferably, $Z^1$ represents a single bond.

Preferably, $Z^2$ represents a single bond.

In an embodiment, A is a 4, 5, 6, 7 or 8-membered ring or two or more fused rings wherein said two or more fused rings preferably consist of 8, 9, 10, 11, 12, 13 or 14 ring atoms.

Preferably, A is an azine moiety, the term "azine" having the meaning defined hereinbelow.

In some preferred embodiments, A is selected from the group consisting of pyrimidine, pyridiazine, pyrazine, triazine and tetrazine and wherein $W^1$ and $W^2$ are the nitrogen atoms of said pyrimidine, pyridazine, pyrazine, triazine or tetrazine ring.

Preferably, A is a selected from the group consisting of pyrimidine, pyridazine, pyrazine and wherein $W^1$ and $W^2$ are the nitrogen atoms of said pyrimidine, pyridazine or pyrazine ring.

In some embodiments, A is a bicyclic, tricyclic or polycyclic fused ring system.

In other embodiments, A may be a bicyclic fused ring system selected from the group consisting of napthyridine, phthalazine, quinoxaline and quinazoline and wherein $W^1$ and $W^2$ are the nitrogen atoms of said bicyclic fused ring system.

In further embodiments, A is tricyclic fused ring system selected from the group consisting of benzocinnoline, benzoquinoxaline, pyridoquinoline, benzoquinazoline and phenazine and wherein $W^1$ and $W^2$ are the nitrogen atoms of said tricyclic fused ring system.

Preferably, $B^1$ and $B^2$ each independently comprise at least one aromatic moiety.

Preferably, $B^1$ has the general formula:

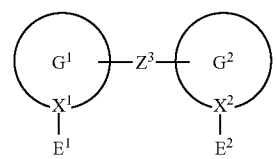

Formula (II)

wherein $G^1$ and $G^2$ represent first and second aromatic moieties respectively and $Z^3$ is one or more bonds or one or more connecting moieties by which the first aromatic moiety $G^1$ is joined to the second aromatic moiety $G^2$; $X^1$ and $X^2$ are defined as above; and $E^1$ and $E^2$ each independently represent a coordination bond to $M^1$.

Preferably, $B^2$ has the general formula:

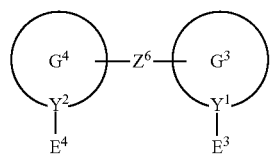

Formula (III)

wherein $G^3$ and $G^4$ represent first and second aromatic moieties respectively and $Z^6$ is one or more bonds or one or more connecting moieties by which the first aromatic moiety $G^3$ is joined to the second aromatic moiety $G^4$; $Y^1$ and $Y^2$ are defined as above; and $E^3$ and $E^4$ each independently represent a coordination bond to $M^2$.

Thus in embodiments of the invention, the complex according to the invention has the general formula:

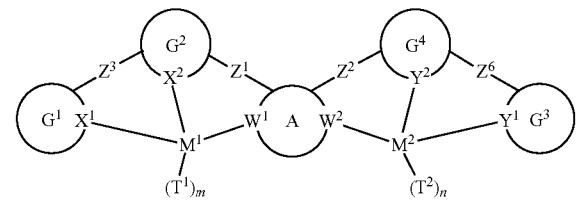

Formula (IV)

wherein each of $M^1$, $M^2$, $X^1$, $X^2$, $Y^1$, $Y^2$, $W^1$, $W^2$, $T^1$, $T^2$, m, n, $G^1$, $G^2$, $G^3$, $G^4$, A, $Z^1$, $Z^2$, $Z^3$ and $Z^6$ is as defined above.

In some preferred embodiments of the invention, the complex according to the invention has the general formula:

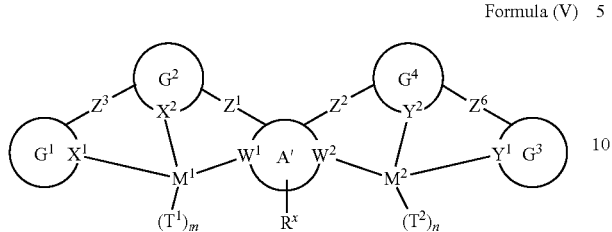

Formula (V)

wherein A' is an aromatic heterocyclic moiety including a six-membered aromatic ring said aromatic ring including coordinating atoms $W^1$ and $W^2$, wherein $R^x$ represents one or more groups selected from: H and a substituent, which substituents may be the same or different; and wherein each of $M^1$, $M^2$, $X^1$, $X^2$, $Y^1$, $Y^2$, $W^1$, $W^2$, $T^1$, $T^2$, m, n, $G^1$, $G^2$, $G^3$, $G^4$, $Z^1$, $Z^2$, $Z^3$ and $Z^6$ is as defined above.

In some preferred embodiments, $R^x$ is H.

Preferably A' is a six-membered aromatic heterocyclic ring which includes coordinating atoms $W^1$ and $W^2$.

Preferably in Formulas (IV) and (V), $W^1$ and $W^2$ each represent nitrogen.

Preferably in Formulas (II), (IV) or (V) said first aromatic moiety $G^1$ is represented by the formula:

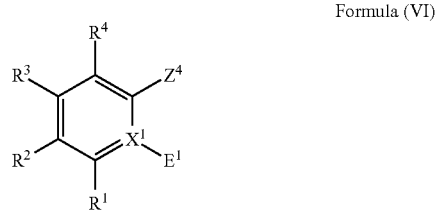

Formula (VI)

wherein $X^1$ is carbon, nitrogen, sulphur or oxygen and preferably carbon or nitrogen; $R^1$, $R^2$, $R^3$ and $R^4$ are each independently selected from the group consisting of: H and a substituent; $Z^4$ represents a bond to $Z^3$, or where $Z^3$ is a bond, is that bond and $E^1$ represents a coordination bond to $M^1$.

Preferably in Formulas (II), (IV) or (V) said second aromatic moiety $G^2$ is represented by the formula:

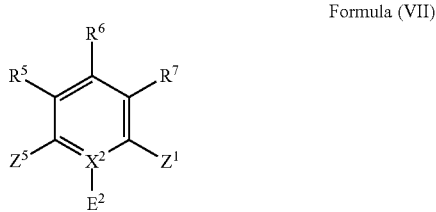

Formula (VII)

wherein $X^2$ is as defined for $X^1$ as above; $R^5$, $R^6$ and $R^7$ are each independently selected from the group consisting of: H and a substituent; $Z^5$ represents a bond to $Z^3$, or where $Z^3$ is a bond, is that bond; $E^2$ represents a coordination bond to $M^2$ and $Z^1$ is defined as above.

Preferably in Formula (III), (IV) or (V) said first aromatic moiety $G^3$ is represented by the formula:

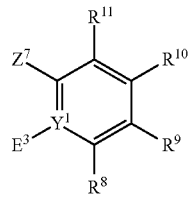

Formula (VIII)

wherein $Y^1$ is as defined for $X^1$ as above; $R^8$, $R^9$, $R^{10}$ and $R^{11}$ are each independently selected from the group consisting of: H and a substituent; $Z^7$ represents a bond to $Z^6$, or where $Z^6$ is a bond, is that bond and $E^3$ represents a coordination bond to $M^2$.

Preferably in Formula (III), (IV) or (V) said second aromatic moiety $G^4$ is represented by the formula:

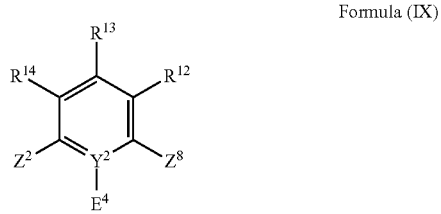

Formula (IX)

wherein $Y^2$ is as defined for $X^1$ as above; $R^{12}$, $R^{13}$ and $R^{14}$ are each independently selected from the group consisting of: H and a substituent; $Z^8$ represents a bond to $Z^6$, or where $Z^6$ is a bond, is that bond; $E^4$ represents a coordination bond to $M^2$ and $Z^2$ is defined as above.

In embodiments of the invention each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may independently be selected from the group consisting of: H, a substituted or unsubstituted hydrocarbyl group, a substituted or unsubstituted hydrocarbyloxy group, hydroxy, carboxy, carboxamido, imino, alkanoyl, ester, amide, cyano, nitro, amino and halogen.

In embodiments of the invention, the complex has the structure:

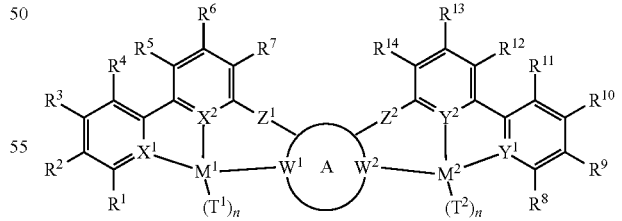

Formula (X)

wherein:

A, $M^1$ and $M^2$, $X^1$ and $X^2$, $Y^1$ and $Y^2$, $Z^1$ and $Z^2$ and $T^1$, $T^2$, m, n, and $R^1$ to $R^{14}$ are defined as above.

In these embodiments, preferably $W^1$ and $W^2$ are nitrogen.

In further embodiments of the invention, the complex has the structure:

Formula (XI)

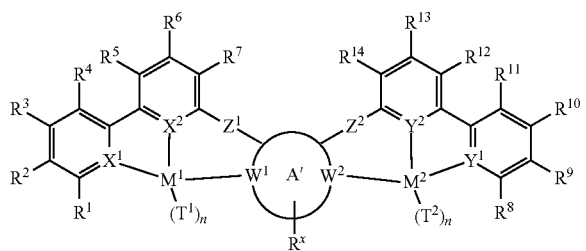

wherein $A^1$, $M^1$ and $M^2$, $X^1$ and $X^2$, $Y^1$ and $Y^2$, $Z^1$ and $Z^2$ and $T^1$, $T^2$, m, n, $R^x$ and $R^1$ to $R^{14}$ are defined as above.

Preferably A' is a six-membered aromatic heterocyclic ring which includes coordinating atoms $W^1$ and $W^2$.

In these embodiments, preferably $W^1$ and $W^2$ are nitrogen.

In embodiments of the invention, A or A' is selected from the group consisting of: pyrimidine, pyridazine, pyrazine, triazine, tetrazine, napthyridine, phthalazine, quinoxaline, quinazoline, benzocinnoline, benzoquinoxaline, pyridoquinoline and benzoquinazoline.

In embodiments of the invention, the complex has the structure:

Formula (XII)

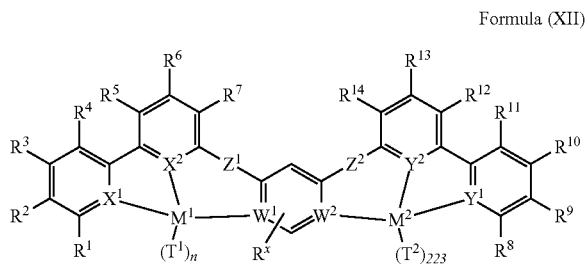

wherein:
$M^1$ and $M^2$, $W^1$ and $W^2$, $X^1$ and $X^2$, $Y^1$ and $Y^2$, $Z^1$ and $Z^2$, $R^x$, $R^1$ to $R^{14}$, $T^1$, $T^2$, m and n are defined as above.

In the embodiments of Formula (XII), preferably $W^1$ and $W^2$ are nitrogen.

Particularly preferably in embodiments of Formulas (X), (XI) and (XII) each of $X^1$, $X^2$, $Y^1$ and $Y^2$ is independently selected from carbon and nitrogen.

Preferably in these Formulas one of $X^1$ and $X^2$ is nitrogen and the other is carbon.

Preferably one of $Y^1$ and $Y^2$ is nitrogen and the other is carbon.

Preferably in embodiments of the invention $R^x$ is independently selected from the group consisting of: H, substituted and unsubstituted hydrocarbyl groups, substituted and unsubstituted hydrocarbyloxy groups, hydroxy, carboxy, carboxamido, imino, alkanoyl, ester, amide, cyano, nitro, amino and halogen.

In embodiments of the invention, $R^1$, $R^2$, $R^3$ and $R^4$ and $R^8$, $R^9$, $R^{10}$ and $R^{11}$ are each independently selected from the group consisting of: H, substituted and unsubstituted hydrocarbyl groups, substituted and unsubstituted hydrocarbyloxy groups, hydroxy, carboxy, carboxamido, imino, alkanoyl, ester, amide, cyano, nitro, amino and halogen.

In embodiments of the invention, $R^1$, $R^2$, $R^3$ and $R^4$ and $R^8$, $R^9$, $R^{10}$ and $R^{11}$ are H.

In embodiments of the invention, $R^5$, $R^6$ and $R^7$ and $R^{12}$, $R^{13}$ and $R^{14}$ are each independently selected from the group consisting of: substituted and unsubstituted hydrocarbyl groups, substituted and unsubstituted hydrocarbyloxy groups, hydroxy, carboxy, carboxamido, imino, alkanoyl, ester, amide, cyano, nitro, amino and halogen.

In embodiments of the invention, $R^5$, $R^6$ and $R^7$ and $R^{12}$, $R^{13}$ and $R^{14}$ are each independently selected from the group consisting of: $C_{1-12}$ alkoxy and halogen.

In embodiments of the invention, $R^5$, $R^7$, $R^{12}$ and $R^{14}$ are halogen and $R^6$ and $R^{13}$ are $C_{1-12}$ alkoxy.

Preferably, the coordinating atoms of $X^1$ and $X^2$ and $Y^1$ and $Y^2$ are each independently selected from the group consisting of nitrogen, carbon, sulphur and oxygen. Most preferably the coordinating atoms of $X^1$ and $X^2$ and $Y^1$ and $Y^2$ are each independently selected from carbon and nitrogen. Preferably at least one of $X^1$ and $X^2$ and at least one of $Y^1$ and $Y^2$ is nitrogen.

In preferred embodiments, $X^1$ is nitrogen and $Y^1$ is nitrogen.

In further preferred embodiments, $X^2$ is carbon and $Y^2$ is carbon.

In other embodiments, $X^1$ is carbon and $Y^1$ is carbon.

In other embodiments, $X^1$ and $Y^1$ are carbon and $X^2$ and $Y^2$ are nitrogen.

In some preferred embodiments, $B^1$ and $B^2$ are the same.

In some preferred embodiments, $Z^1$ and $Z^2$ each represent a single bond.

In such embodiments, the complex may be used in an organic light emitting diode. In other aspects, the invention relates to an organic light emitting diode comprising the complex as defined herein.

BRIEF DESCRIPTION OF THE DRAWINGS

Embodiments of the invention are further described hereinafter with reference to the accompanying drawings, in which.

DETAILED DESCRIPTION

Figure 1:
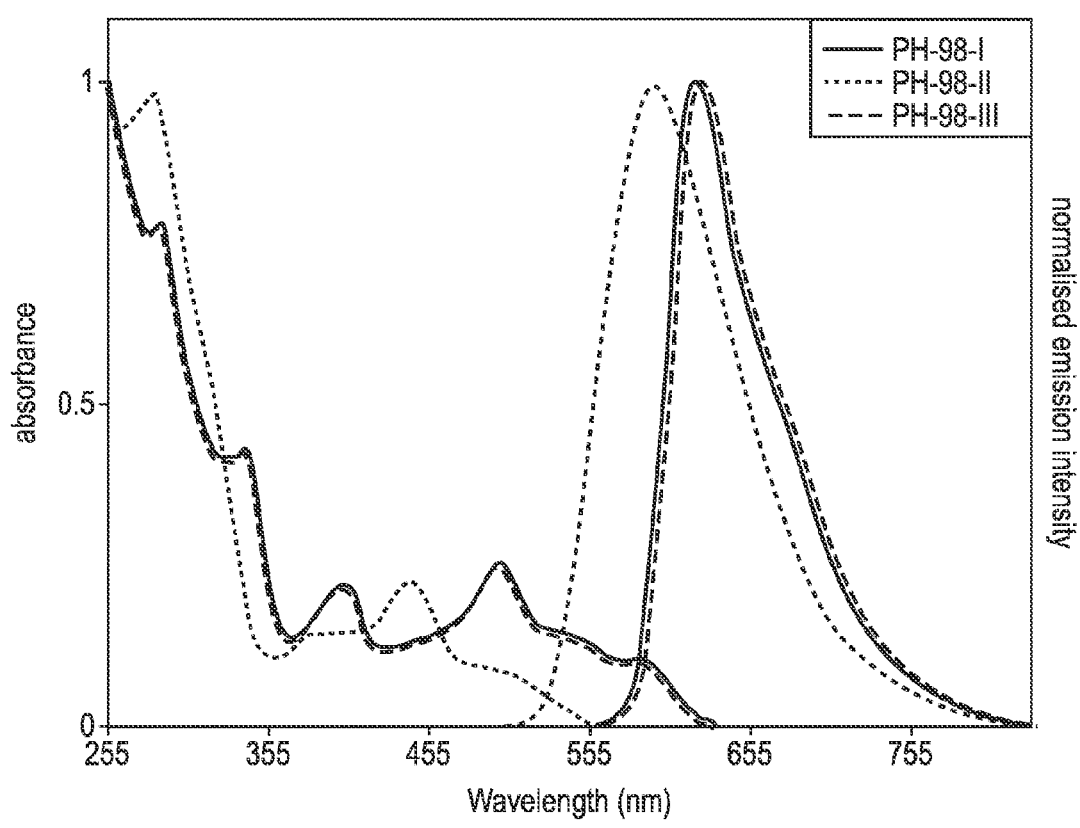
FIG. 1 shows absorption and emission spectra for the monoiridum complex PH-98-II and di-iridium complexes PH-98-I and PH-98-III at room temperature.

For convenience, carbon atom ranges disclosed in this specification are defined by reference to the end points of the range. However, all intermediate carbon atom numbers of any specifically mentioned range are also disclosed. Thus, $C_{1-6}$ means a moiety having 1, 2, 3, 4, 5 or 6 carbon atoms, $C_{1-4}$ means a moiety having 1, 2, 3 or 4 carbon atoms, $C_{3-6}$ means a moiety having 3, 4, 5 or 6 carbon atoms and $C_{1-3}$ means a moiety having 1, 2 or 3 carbon atoms.

The term "each independently selected from the group comprising" or "each independently selected from the group consisting of" or grammatical or linguistic equivalents or variations thereof is intended to mean that each of the listed 'R' groups may be selected from the group independently of the other 'R' groups (here the term 'R' group refers to any group R, $R^x$, $R^1$, $R^2$, $R^3$, $R^4$, $R^5$, $R^6$, $R^7$, $R^8$, $R^9$ etc.). Therefore, each 'R' group may be the same as or different from any other 'R' group. For the avoidance of doubt, the phrase "$R^1$ and $R^2$ are each independently selected from the group consisting of: H and a substituent" covers the following cases in which (1) $R^1$ is H and $R^2$ is a substituent, (2) $R^2$ is H and $R^1$ is a substituent, (3) $R^1$ is H and $R^2$ is H and (4) $R^1$ is a substituent and $R^2$ is a substituent. When $R^1$ is a substituent and $R^2$ is a substituent, $R^1$ and $R^2$ may be the same substituents or may be different substituents since they are each "independently selected" R groups. The same applies to other pairs or combinations of 'R' groups.

Throughout this specification unless specified otherwise, whenever a specific value is quoted for a temperature, pressure or time, the temperature, pressure or time quoted is approximate rather than the precise temperature, amount of pressure or amount of time.

The term "substituent", unless specified otherwise, means a non-hydrogen moiety, for example a hydroxy, carboxy, carboxamido, imino, alkanoyl, cyano, cyanomethyl, nitro, amino, halogen (e.g. fluoro, chloro or bromo), $C_{1-12}$ haloalkyl (e.g. trifluoromethyl), $C_{1-12}$ alkoxy (e.g. methoxy, ethoxy or propoxy), $C_{1-12}$ haloalkoxy (e.g. trifluoromethoxy), hydrocarbyl or hydrocarbyloxy group. The just mentioned groups included in the definition of the term "substituent" may be each independently unsubstituted or substituted (wherever chemically possible and appropriate) with from 1 to 11 substituents selected from the group consisting of: hydroxy, carboxy, carboxamido, imino, alkanoyl, cyano, cyanomethyl, nitro, amino, halogen (e.g. fluoro, chloro or bromo), $C_{1-12}$ alkyl (e.g. methyl, ethyl or propyl), $C_{1-12}$ haloalkyl (e.g. trifluoromethyl), $C_{1-12}$ alkoxy (e.g. methoxy, ethoxy or propoxy), $C_{1-12}$ haloalkoxy (e.g. trifluoromethoxy), $C_{3-6}$ cycloalkyl (e.g. cyclohexyl), aryl (e.g. phenyl), aryl-$C_{1-12}$ alkyl (e.g. benzyl) or $C_{1-12}$ alkyl aryl.

Any compound within the scope of general Formula (I) and having a substituent or substitution which has a materially adverse effect on the light emitting properties of the compound (as compared to a compound which is otherwise identical but lacks said substituent or substitution) is excluded from the scope of the present invention.

Hydrocarbyl and hydrocarbyloxy groups disclosed herein may have, for example, from 1 to 12, e.g. from 1 to 6 carbon atoms.

Exemplary hydrocarbyl groups include those consisting of one or a combination of moieties selected from: alkyl, cycloalkyl, alkenyl, cycloalkenyl and aryl (e.g. phenyl), as is the case of phenylalkyl groups. For example, the term "hydrocarbyl" may be a non-hydrogen group selected from the group consisting of: alkyl (e.g. $C_{1-12}$ alkyl); alkenyl (e.g. $C_{2-12}$ alkenyl); aryl (e.g. phenyl); cycloalkyl (e.g. $C_{3-6}$ cycloalkyl); cycloalkenyl (e.g. $C_{4-6}$ cycloalkenyl); alkyl alkenyl (e.g. $C_{1-12}$ alkyl $C_{2-12}$ alkenyl), alkenyl alkyl (e.g. $C_{2-12}$ alkenyl $C_{1-12}$ alkyl), aryl alkyl (e.g. phenyl $C_{1-12}$ alkyl, such as benzyl); alkyl aryl (e.g. $C_{1-12}$ alkyl phenyl), alkyl cycloalkyl (e.g. $C_{1-12}$ alkyl $C_{3-6}$ cycloalkyl), cycloalkyl alkyl (e.g. $C_{3-6}$ cycloalkyl $C_{1-12}$ alkyl); cycloalkenyl alkyl (e.g. $C_{4-6}$ cycloalkenyl $C_{1-12}$ alkyl), and alkyl cycloalkyl (e.g. $C_{1-12}$ alkyl $C_{3-6}$ cycloalkyl). The above mentioned hydrocarbyl groups may be optionally interrupted by —O—, —S— or —NR—.

It should be noted that the present invention is not limited to a particular subset of substituents and the skilled person may select the combination of substituents to modify the properties of the compound. For example, the colour of the emitted light may be tuned by selecting substituents with specific absorption and emission characteristics.

The present invention provides a compound having a first tridentate ligand portion coordinated with a first metal and a second tridentate ligand portion coordinated with a second metal. The incorporation of respective tridentate ligand portions to coordinate the first and second metal atoms $M^1$ and $M^2$ ensures the synthesis of compounds of the present invention is both easier and more efficient than the synthesis of related compounds of the prior art. This is in contrast to, for example, the synthesis of cyclometallated octahedral complexes with two metal centres wherein each metal atom is respectively coordinated to three bidentate ligands. Complexes of this latter type are chiral and their synthesis may result in mixtures containing diastereomers with different physical and chemical properties. The synthesis of such complexes is inefficient and because a mixture is obtained with non-uniform properties, additional laborious separation steps may be required to isolate only those compounds with the requisite properties. Contrary to this, the synthesis of compounds of the present invention results in a non-chiral compound, a single enantiomer (right handed or left handed) or a mixture of enantiomers (right handed and left handed). Consequently, the properties of the compounds obtained are uniform. No diastereomers with different chemical and physical properties are therefore produced and where mixtures of enantiomers are obtained, these can easily be resolved.

The compounds of the present invention are luminescent and thus are able to emit light as a result of the excitation of atoms by energy other than heat. More particularly, the compounds of the invention are phosphorescent, wherein phosphorescence is defined as the emission of radiation that occurs when there is a change in spin multiplicity between a triplet excited state and a singlet ground state.

The compounds of the present invention are able to achieve as high, if not higher, quantum efficiency than those compounds of the prior art which the inventors believe are structurally related. Notably, compounds of the invention exhibit a luminescent quantum yield of greater than 59% at wavelengths around 622 nm and 625 nm. Particularly, compounds of the invention can exhibit a luminescent quantum yield of greater than 60% and specifically a luminescent quantum yield of 65% at wavelengths around 622 nm and 625 nm.

The compounds of the present invention are cyclometallated organometallic complexes. As the complexes of the invention are organometallic, they comprise at least one carbon-metal bond to enable coordination of the ligand moiety to the metal atom. Typically, the carbon-metal bond is a covalent bond. The presence of an organometallic carbon-metal bond defining the coordination of the metal atom with the ligand moiety thus distinguishes the complexes of the invention from coordination polynuclear complexes of the prior art which do not exhibit such a organometallic bonding arrangement.

In embodiments of the invention, at least one of $X^1$, $X^2$, $Y^1$ and $Y^2$ is carbon. In certain embodiments, at least one of $X^1$ and $X^2$ is carbon and at least one of $Y^1$ and $Y^2$ is carbon. Thus in some embodiments, the complexes of the invention may comprise at least two carbon-metal bonds for coordination with the respective metal atoms $M^1$ and $M^2$. The first tridentate ligand portion and the second tridentate ligand portion can therefore each be connected to their respective metal atoms $M^1$ and $M^2$ by means of metal-carbon covalent bonds.

In embodiments of the invention, $W^1$ and $W^2$ are each independently selected from the group consisting of nitrogen, sulphur and oxygen. In much preferred embodiments, $W^1$ and $W^2$ are nitrogen.

In preferred embodiments of the invention, $M^1$ and $M^2$ are transition metals. Typically, $M^1$ and $M^2$ are second and third row transition metals but could be any other transition metal with which luminescent properties may be obtained. In preferred embodiments, $M^1$ and $M^2$ are each independently selected from the group consisting of iridium, platinum, palladium, osmium, rhenium, ruthenium and gold.

In an embodiment, $M^1$ and $M^2$ are the same. In one embodiment $M^1$ and $M^2$ are iridium. In other embodiments, compounds of the present invention may comprise mixed metal centres wherein $M^1$ and $M^2$ are different. In one particular embodiment, one of $M^1$ and $M^2$ is iridium and the other is platinum. The invention is not necessarily limited in this regard and $M^1$ and $M^2$ could comprise other combinations of transition metals and particularly any combination of those transition metals listed above.

In some preferred embodiments, $M^1$ and $M^2$ are each independently selected from iridium and platinum. Compounds of the invention containing iridium and/or platinum as metal centres advantageously demonstrate particularly high luminescent quantum yields.

The compounds of the present invention comprise an aromatic heterocyclic moiety, A, containing coordinating heteroatoms $W^1$ and $W^2$. The aromatic heterocyclic moiety links the first metal centre, $M^1$, to the second metal centre, $M^2$. The incorporation of the aromatic moiety strongly connects the metal centres. Crucially, the linkage group A is rigid such that $M^1$ cannot rotate with respect to $M^2$. The heterocyclic aromatic linkage in this configuration encourages the compound to behave as a single luminophore. Thus the aromatic heterocyclic moiety, A, can be represented by any of a number different moieties providing the moiety contains heteroatoms to coordinate to the metal atoms, $M^1$ and $M^2$, and maintains a rigid planar configuration between the metal atoms.

In an embodiment, A is a 4, 5, 6, 7 or 8-membered ring. In another embodiment, A comprises two or more fused rings wherein said two or more fused rings preferably consist of 8, 9, 10, 11, 12, 13 or 14 ring atoms. By means of example, the two fused rings of a napthyridine moiety consist of 10 atoms.

In a preferred embodiment, A is an azine moiety wherein azine is defined as an organic compound having a six-membered aromatic ring and wherein the aromatic ring comprises at least one nitrogen atom. In embodiments of the invention, A is selected from the group consisting of pyrimidine, pyridazine, pyrazine, triazine and tetrazine. In such embodiments, moiety A comprises at least two nitrogen atoms. When A is selected from pyrimidine, pyridazine or pyrazine, A comprises two nitrogen atoms as part of the pyrimidine, pyridazine or pyrazine ring and $W^1$ and $W^2$ are those nitrogen atoms. When A is selected from triazine and tetrazine, A comprises more than two nitrogen atoms as part of the triazine and tetrazine ring and $W^1$ and $W^2$ may be respectively any suitably located two nitrogen atoms forming part of the triazine or tetrazine ring.

In embodiments wherein A comprises a fused ring system, A may comprise a bicyclic, tricyclic or polycyclic fused ring system.

In embodiments wherein A comprises a bicyclic fused ring system, A may be selected from the group consisting of napthyridine, phthalazine, quinoxaline and quinazoline. In such embodiments, A comprises two nitrogen atoms as part of the napthyridine, phthalazine, quinoxaline or quinazoline bicyclic ring system and $W^1$ and $W^2$ are those nitrogen atoms. For example, A may have the core structure comprising the following wherein lines extending from $W^1$ and $W^2$ represent coordinate bonds to the metal atoms $M^1$ and $M^2$ respectively and lines extending from either aromatic ring represent a bond or connecting moieties by which the bicyclic ring system is joined to each tridentate ligand portion:

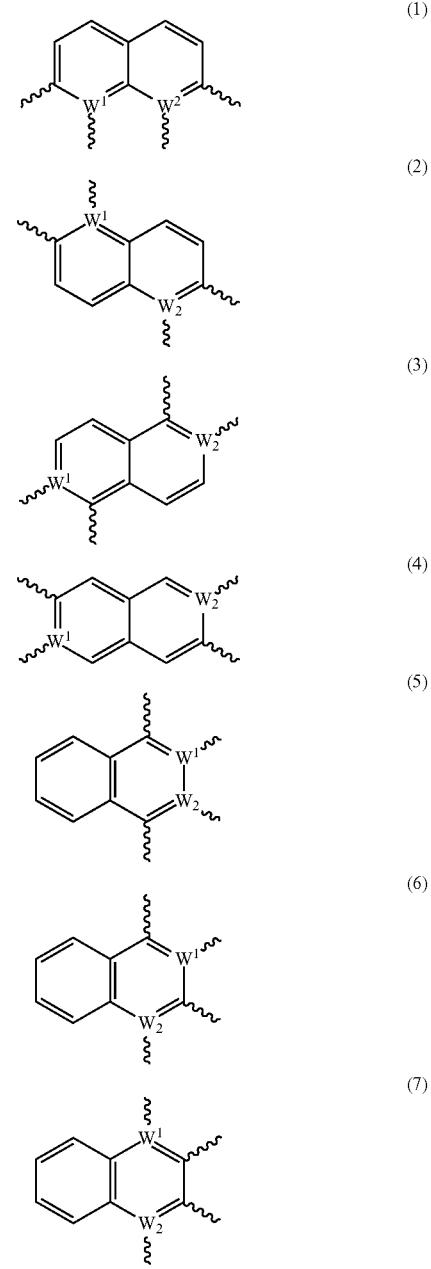

The structures numbered (1) to (4) represent alternative isomeric forms of the aromatic heterocyclic moiety when A is a napthyridine. Structure (5) represents a phthalazine, (6) is a quinazoline and (7) is a quinoxaline. Further configurations or arrangements based on these structures are not precluded and the invention is not to be limited in this regard.

In embodiments wherein A comprises a tricyclic fused ring system, A may be selected from the group consisting of pyridoquinoline, benzoquinoxaline and benzoquinazoline. In such embodiments, A comprises two nitrogen atoms as part of the pyridoquinoline, benzoquinoxaline and benzoquinazoline tricyclic ring system and $W^1$ and $W^2$ are those nitrogen atoms. For example, A may have the core structure comprising the following wherein lines extending from $W^1$ and $W^2$ represent bonds to the metal atoms $M^1$ and $M^2$ respectively and lines extending from an aromatic ring represent a bond or connecting moieties by which the tricyclic ring system is joined to each tridentate ligand portion:

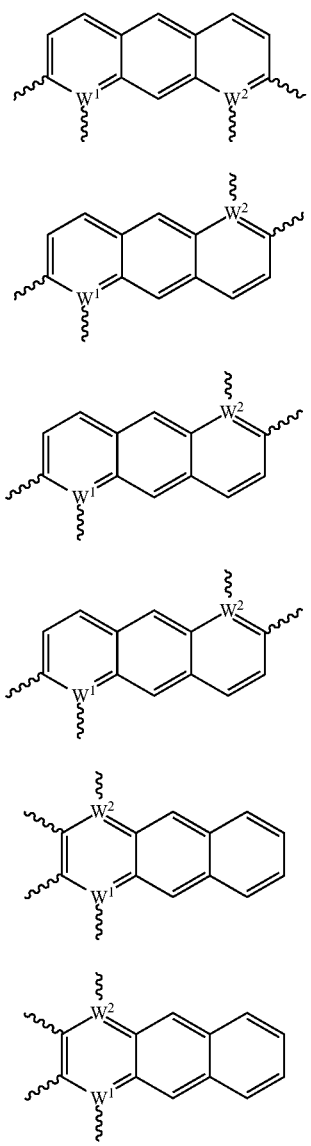

The structures numbered (8) to (11) represent alternative isomeric forms of the aromatic heterocylic moiety when A is a pyridoquinoline. Structure (12) represents a benzoquinazoline and (13) represents a benzoquinoxaline. Further configurations or arrangements based on these structures are not precluded and the invention is not to be limited in this regard.

In other embodiments A may comprise a tricyclic fused ring system wherein A is selected from benzocinnoline or phenazine. In yet other embodiments A may comprise a polycyclic fused ring system, wherein A is formed from more than three fused rings.

In positions at which the aromatic heterocyclic moiety A is not coordinated to a metal atom or joined to the rest of a terdentate ligand portion, A may be substituted with hydrogen to the extent necessary to satisfy the valence of the atoms at such positions. Alternatively, A may comprise one or more substituents in such positions.

In embodiments of the invention, the coordinating atoms of $X^1$ and $X^2$ and $Y^1$ and $Y^2$ are each independently selected from the group consisting of nitrogen, carbon, sulphur and oxygen. In preferred embodiments, the coordinating atoms of $X^1$ and $X^2$ and $Y^1$ and $Y^2$ are each independently selected from carbon and nitrogen.

In one embodiment each tridentate ligand portion bridges the metal to which it is attached in a C^N^N coordination mode. In such embodiments, $X^1$ and $Y^1$ are carbon, $X^2$ and $Y^2$ are nitrogen and $W^1$ and $W^2$ are nitrogen.

In other embodiments, each tridentate ligand portion bridges the metal to which it is attached in a C^C^N coordination mode. In such embodiments, $X^1$ and $X^2$ are carbon, $Y^1$ and $Y^2$ are carbon and $W^1$ and $W^2$ are nitrogen.

In preferred embodiments each tridentate ligand portion bridges the metal to which it is attached in an N^C^N coordination mode. In such preferred embodiments, $X^1$ and $Y^1$ are nitrogen, $X^2$ and $Y^2$ are carbon and $W^1$ and $W^2$ are nitrogen.

In some embodiments, $B^1$ and $B^2$ are the same.

In other embodiments, $B^1$ and $B^2$ are different. When $B^1$ and $B^2$ are different, the arrangement of corresponding coordinating atoms $W^1$ and $W^2$, $X^1$ and $X^2$ and $Y^1$ and $Y^2$ may follow the same pattern such that each tridentate ligand portion adopts the same coordination mode (e.g. N^C^N and N^C^N).

Alternatively, one of the corresponding coordinating atoms $W^1$ and $W^2$, $X^1$ and $X^2$ and $Y^1$ and $Y^2$ may be different such that the first tridentate ligand portion adopts one coordination mode with the first metal centre (e.g. N^C^N) and the second tridentate ligand portion adopts a different coordination mode with the second metal centre (e.g. C^N^N).

In some embodiments of the invention, $R^5$, $R^6$ and $R^7$ and $R^{12}$, $R^{13}$ and $R^{14}$ are each independently selected from the group consisting of: $C_{1-6}$ alkoxy and halogen.

In some embodiments of the invention, $R^6$ and $R^{13}$ are $C_{1-6}$ alkoxy.

In some embodiments of the invention, $R^6$ and $R^{13}$ are hexyloxy.

In some embodiments of the invention, $R^5$, $R^7$, $R^{12}$ and $R^{14}$ are halogen.

In some embodiments of the invention, $R^5$, $R^7$, $R^{12}$ and $R^{14}$ are fluorine.

In some embodiments of the invention, $R^6$ and $R^{13}$ are halogen.

In some embodiments of the invention, $R^6$ and $R^{13}$ are fluorine.

In some embodiments of the invention, $Z^1$ and $Z^2$ each represent a single bond.

The compounds of the present invention may comprise auxiliary ligands $T^1$ and $T^2$. The auxiliary ligands $T^1$ and $T^2$ may be the same or different. The number of auxiliary ligands is dependent on the coordination requirements of the metal centre. For example, the metal centre in embodiments of the invention wherein the metal is iridium will be hexacordinate. The auxiliary ligands required to satisfy the coordination requirements of a hexacordinate metal species could therefore comprise a tridentate ligand, a bidentate ligand and a monodentate ligand, or three monodentate ligands. If the cyclometallated complex in accordance with the present invention comprises two hexacoordinate metal species, such as two iridium metal centres, a number of combinations of auxiliary ligands are possible. By means of illustration, the complex could comprise two tridentate ligands each coordinated respectively to $M^1$ and $M^2$, two bidentate ligands and a monodentate ligand coordinated to $M^1$ and two bidentate ligands and a monodentate ligand coordinated to $M^2$ or three monodentate ligands coordinated to $M^1$ and three monodentate ligands coordinated to $M^2$. The above-described alternatives are of course not exhaustive and other combinations of respective tridentate, bidentate and monodentate ligands at each metal centre will be possible (for example, a tridentate ligand could be coordinated to $M^1$ and a bidentate ligand and a monodentate ligand could be coordinated to $M^2$). Alternatively, the metal centre in embodiments of the invention wherein the metal is platinum will be tetracoordinate. In this particular case the auxiliary ligand may comprise a single monodentate ligand coordinated to the metal. Thus for embodiments of the invention comprising two platinum metal centres, a single monodentate ligand will be coordinated respectively to $M^1$ and $M^2$. For embodiments of the invention comprising mixed metal centres, each metal having a different coordination requirement (for example iridium and platinum), various combinations of ligands to satisfy the respective coordination requirements will again be possible. Thus it will be understood by the skilled practitioner that a variety of combinations of tridentate, bidentate and monodentate auxiliary ligands are foreseeable depending on the respective coordination requirements at each metal centre and the invention is not to be limited to any particular set of combinations in this regard.

Suitable tridentate ligands may be selected from, but are not limited to, the list consisting of: 2,2':6',2''-terpyridine (tpy), 2,6-diphenylpyridine, 2,6-pyridinedicarboxylate, 6-phenyl-2-pyridinecarboxylic acid and 2,6-bis(2-benzimidazoyl)pyridine Suitable bidentate ligands may be selected from, but are not limited to, the list consisting of: 2-(p-tolyl)pyridine, 2,2'-bipyridine, acetylacetonate and 2-pyridinecarboxylic acid.

Suitable monodentate ligands may be selected from, but are not limited to, the list consisting of: chloride, bromide, iodide, cyano, thiocyanato, carbon monooxide, azido, phenolate, alkynyl and dimethyl sulfoxide.

In an embodiment, 2-(p-tolyl)pyridine is coordinated to $M^1$ and/or $M^2$.

In an embodiment, chloride is coordinated to $M^1$ and/or $M^2$.

In an embodiment, 2-(p-tolyl)pyridine and chloride are coordinated to $M^1$ and/or $M^2$.

The invention will now be exemplified by reference to the following examples:

Example 1

PH-98-I and PH-98-III

Di-iridium compounds PH-98-I and PH-98-III were synthesized according to the following reaction scheme:

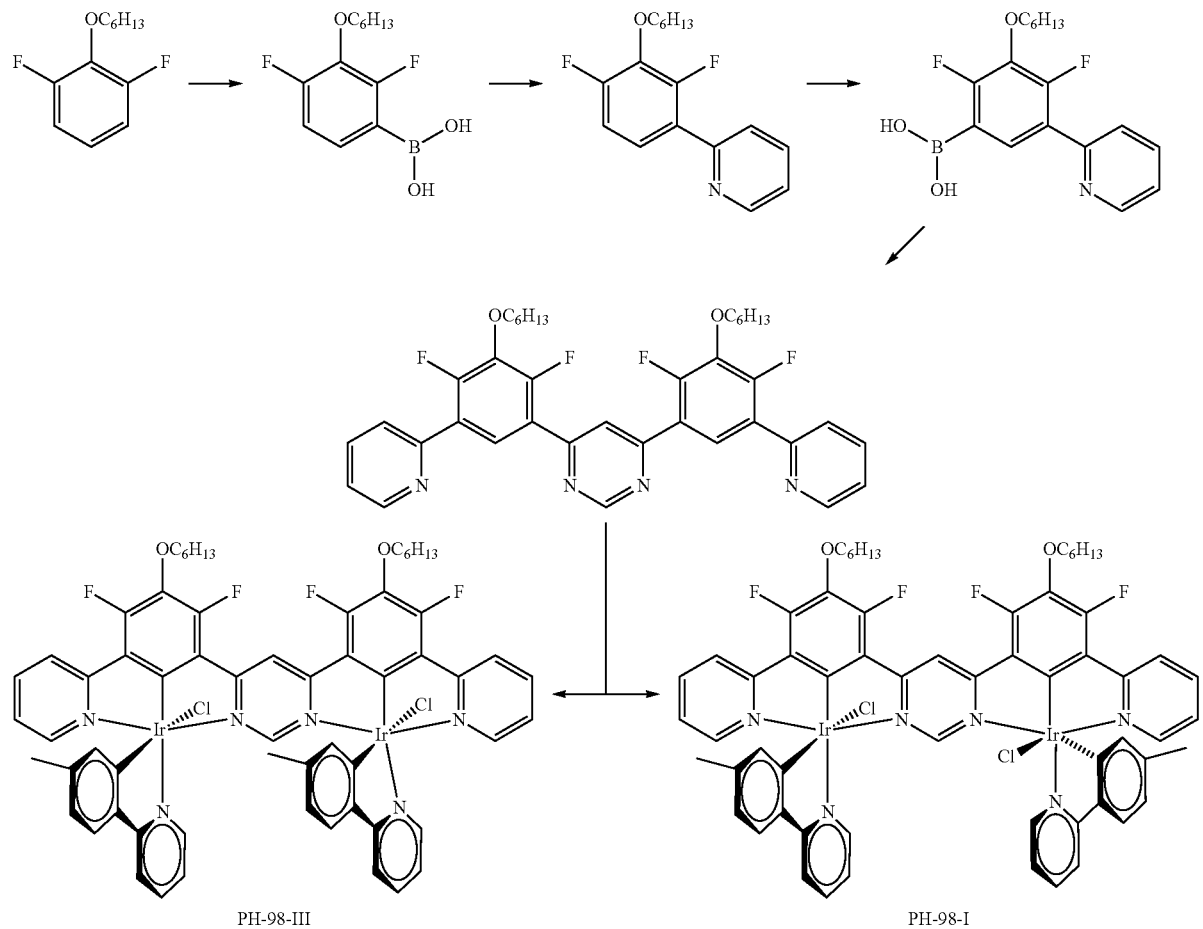

PH-98-III    PH-98-I

Synthesis of 2,4-difluoro-3-hexyloxybenzene (PH-34)

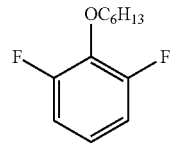

A mixture of K$_2$CO$_3$ (33 g, 770 mmol), acetonitrile (100 mL), 2,4-diflurophenol (5 g, 38 mmol), 1-bromohexane (6 mL, 45.5 mmol), and a catalytic amount of sodium iodide was heated under reflux for 14 hours. After cooling to room temperature, brine (60 mL) and ethyl acetate were added, layers were separated and the aqueous layer was treated with more ethyl acetate (3×30 mL). The combined organic layers were dried over anhydrous MgSO$_4$, filtered and evaporated to dryness. No further purification is required before the next step. Colourless oil (7.77 g, 95%). $^1$H NMR (400 MHz, CDCl$_3$) δ 6.89 (m, 3H), 4.11 (t, 2H, J=6.1 Hz); 1.74 (q, 2H, J=7.1 Hz); 1.45 (m, 2H); 1.32 (m, 4H); 0.89 (t, 3H, J=6.1 Hz). $^{13}$C NMR (68 MHz, CDCl$_3$) 157.66 (d, J=5.7 Hz), 155.19 (d, J=5.7 Hz), 122.56 (dd, J=9.0 Hz), 112.17 (m), 74.90, 31.60, 29.99, 25.39, 22.66, 14.09.

Synthesis of 2,4-difluoro-3-hexyloxyphenyl boronic acid (PH-46)

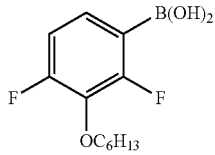

To a stirred solution of 2,4-difluoro-3-hexyloxybenzene (6 g, 28 mmol) in dry THF (50 mL), at −78° C., n-butyllithium (1.6 M solution in hexane, 20 mL, 32 mmol) was added slowly. Solution was stirred at −78° C. for 2 hours. Triisopropylborate (7.7 mL, 30.8 mmol) was added slowly and the mixture was stirred over night. During this time the temperature slowly reached room temperature. The mixture was acidified by addition of 4M aqueous hydrochloric acid. Brine (30 mL) was added, layers separated and the aqueous layer was extracted with ethyl acetate. Combined organic layers were dried over MgSO$_4$ and all volatile components were removed by rotary evaporation under reduced pressure. The product was then purified by column chromatography (SiO$_2$, petroleum ether/ethyl acetate, 1/1). NMR spectra are not well resolved.

Synthesis of 2-(2,4-difluoro-3-hexyloxyphenyl)pyridine (PH-39)

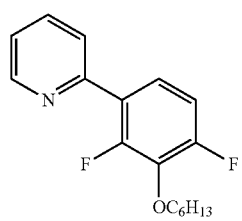

A mixture of 2,4-difluoro-3-hexyloxyphenyl boronic acid (3.50 g, 13.6 mmol), 2-bromopyridine (1.79 g, 11.3 mmol), potassium carbonate (7.51 g, 54.4 mmol), toluene (25 mL), ethanol (2 mL) and water (18 mL) was deoxygenated by bubbling nitrogen through the mixture for 20 minutes. Pd(PPh$_3$)$_4$ (618 mg, 0.6 mmol) was added and the mixture was heated under reflux for 15 hours. Brine (30 mL) was added and the layers separated. Aqueous layer was extracted with ethyl acetate (3×20 mL). Combined organic layers were dried over MgSO$_4$, filtered and the solvent was removed by rotary evaporation under reduced pressure. The product was purified by column chromatography (SiO$_2$, Hexane/EtOAc, from 9/1 to 7/3, v/v) to give the desired product as colourless oil (2.98 g, 76%). $^1$H NMR (270 MHz, CD$_2$Cl$_2$) δ 8.69 (ddd, 1H, J=4.8 Hz, J=1.7 Hz, J=1.8 Hz, J=1.2 Hz), 7.76 (m, 2H), 7.64 (ddd, 1H, J=9.0 Hz, J=8.2 Hz, J=6.2 Hz), 7.27 (ddd, 1H, J=6.8 Hz, J=4.9 Hz, J=2.0 Hz), 7.02 (ddd, 1H, J=10.0 Hz, J=9.0 Hz, J=2.0 Hz), 4.15 (t, 2H, J=13.2 Hz), 1.77 (q, 2H, J=6.8 Hz), 1.47 (m, 2H), 1.33 (m, 4H), 0.91 (m, 3H). $^{13}$C NMR (68 MHz, CD$_2$Cl$_2$) δ 173.45, 160.08, 147.73 (m), 146.17, 126.00, 135.78 (d, J=54.4 Hz), 435.49 (d, J=5.4 Hz), 98.81 (dd, J=4.2 Hz), 55.20, 53.63, 49.01, 46.26, 37.46, 23.25.

Synthesis of 2,4-difluoro-3-hexyloxy-5-(2-pyridyl)phenyl boronic acid (PH-40)

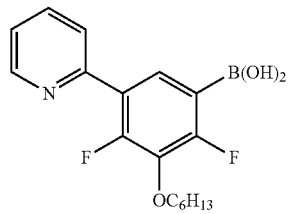

n-Butyllithium (1.6 M solution in hexane, 7.6 mL, 12.2 mmol) was added slowly with stirring to a solution of 2-(2,4-difluoro-3-hexoxybenzene)pyridine (2.978 g, 10.2 mmol) and N,N,N'N',N-pentamethyldiethylenetriamine (2.13 mL, 10.2 mmol) in dry THF (20 mL) at −78° C. Solution was stirred at −78° C. for 2 hours. Triisopropylborate (2.8 mL, 12.2 mmol) was added slowly and the mixture was allowed to warm to room temperature over a period of 14 hours. The mixture was neutralised by addition of diluted acetic acid. Brine (15 mL) was added, layers separated and the aqueous layer was extracted with ethyl acetate (3×15 mL). Combined organic layers were dried over MgSO$_4$, filtered and all volatiles were removed under reduced pressure. The crude product was used in the next step without further purification. $^1$H NMR (270 MHz, CDCl$_3$) δ 8.85 (d, 1H, J=5.3 Hz); 8.31 (dd, 1H, J=8.2 Hz); 8.01 (d, 1H, J=7.8 Hz); 7.59 (m, 2H); 4.13 (t, 2H, J=6.4 Hz); 1.72 (m, 2H); 1.43 (m, 2H); 1.33 (m, 4H); 0.86 (t, 3H, J=7.0 Hz).

Synthesis of Bisterdentate Ligand PH-45

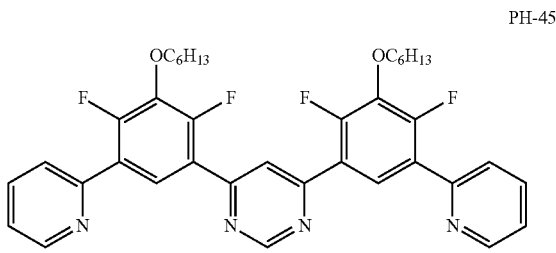

PH-45

A mixture of $K_2CO_3$ (1.656 g, 12 mmol), 2,4-difluoro-3-hexyloxy-5-(2-pyridyl)phenyl boronic acid (1 g, 3 mmol) and 4,6-dichloropyrimidine (186 mg, 1.25 mmol) water (5 mL), toluene (7 mL) and ethanol (1 mL) was deoxygenated by bubbling $N_2$ through the mixture for 20 minutes. $Pd(PPh_3)_4$ (103 mg, 0.1 mmol) was then added and the mixture was heated under refluxed for 15 hours. Brine (15 mL) was added and the phases were separated. The aqueous layer was extracted with ethyl acetate (3×10 mL). The combined organic layers were dried over $MgSO_4$, filtered and evaporated to dryness. The product was purified by column chromatography ($SiO_2$, Heptane/EtOAc, form 9/1 to 7/3). Colourless solid (672 mg, 82%). mp $^1$H NMR (270 MHz, toluene-$d_8$) δ 9.30 (d, 1H, J=1.4 Hz), 9.15 (dd, 2H, J=8.6 Hz), 8.54 (ddd, 2H, J=4.9 Hz, J=2 Hz, J=0.7 Hz), 8.39 (d, 1H, J=1.5 Hz), 7.59 (ddd, 2H, J=7.9 Hz, J=2 Hz, J=0.7 Hz), 7.14 (ddd, 2H, J=9.6 Hz, J=7.6 Hz), 6.67 (ddd, 2H, J=7.6 Hz, J=4.9 Hz, J=1.2 Hz), 2.08 (m, 4H), 1.69 (m, 4H), 1.41 (m, 4H), 1.26 (m, 8H), 0.90 (dd, 6H, J=6.7 Hz). $^{13}$C NMR (68 MHz, toluene-$d_8$) δ 160.0, 159.2, 158.1, 158.0, 157.8, 157.7, 154.3, 154.1, 153.9, 152.3, 149.9, 135.8, 128.2, 127.7, 127.3, 75.2, 31.7, 30.2, 25.5, 22.8, 19.6.

Synthesis of PH-98-II

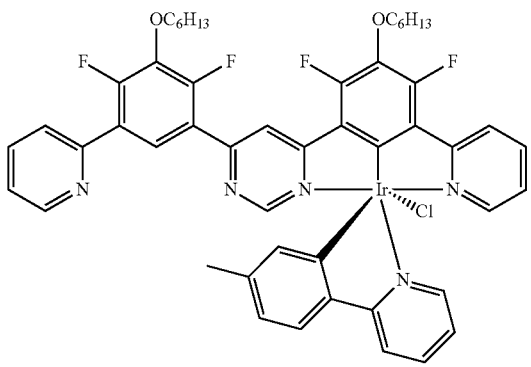

PH-98-II

A mixture of PH-45 (200 mg, 0.3 mmol), 2-ethoxyethanol (15 mL), water (5 mL) and $IrCl_3*nH_2O$ (110 mg, 0.3 mmol) was heated under reflux for 12 hours. After cooling to room temperature, water was added and the formed dark orange precipitate was filtered off. The solid was washed with water and dried. To this solid, 2-(p-tolyl)pyridine (2 ml, excess) and AgOTf (234 mg, 0.91 mmol) were added and the mixture was stirred at 115° C. for 10 h. The mixture was treated with DCM and brine. The aqueous layer was extracted 3 times with DCM, the combined organic layer was dried over $MgSO_4$, filtered and DCM was removed by rotary evaporation. The excess of 2-(p-tolyl)pyridine was distilled off in vacuum (160° C., 2 mmHg). The residue was applied to a column (silica gel DCM). The column was first eluted with pure DCM followed by a mixture of DCM/ethylacetate, 3/2). Fractions containing the product were combined and evaporated to dryness to give the monoiridium complex. Yield (162 mg, 51%). HRMS for $[C_{50}H_{47}F_4IrN_5O_2]^+$ calcd. 1018.3295. found 1018.3285. Elemental Analysis calcd for $C_{50}H_{47}F_4IrN_5O_2Cl$ C, 57.00%; H, 4.50%; N, 6.65%. found C, %; H, %; N, %. $^1$H NMR ($CDCl_3$, 400 MHz) δ 10.07 (dd, 1H, J=0.9 Hz, J=5.5 Hz), 8.67 (d, 1H, J=4.9 Hz), 8.50 (s, 1H), 8.35 (dd, 1H, J=8.2 Hz), 8.26 (s, 1H), 8.13 (d, 1H, J=8.2 Hz), 8.03 (d, 1H, J=8.2 Hz), 7.96 (ddd, 1H, J=1.5 Hz, J=7.8 Hz), 7.73 (m, 2H), 7.65 (m, 2H), 7.51 (m, 2H), 7.25 (ddd, 1H, J=1.8 Hz, J=5.0 Hz, J=6.8 Hz), 6.89 (ddd, 1H, J=1.4 Hz, J=4.6 Hz, J=6.0 Hz), 6.60 (dd, 1H, J=1 Hz, J=7.8 Hz), 5.76 (s, 1H), 4.22 (m, 4H), 1.87 (m, 7H), 1.51 (m, 10H), 0.94 (m, 6H). $^{13}$C NMR ($CDCl_3$, 100 MHz) δ 178.57, 173.09, 173.04, 165.96, 164.77, 159.50, 158.41, 157.25 (dd, J=5 Hz, J=51 Hz), 156.73, 156.63, 154.74 (dd, J=5 Hz, J=51 Hz), 152.07, 151.30, 150.01, 149.57, 144.49, 140.76, 139.98, 138.04, 137.27, 136.60, 136.49, 130.06, 129.87, 125.03 (dd, J=3 Hz, 10 Hz), 124.45, 124.24, 124.15, 124.11, 123.49, 123.36, 123.00, 122.86, 122.51, 122.21 (d, J=3 Hz), 121.01 (dd, J=4 Hz, J=8 Hz), 117.77, 117.33 (dd, J=10 Hz), 75.71, 75.61, 31.75, 31.62, 30.21, 30.08, 25.63, 25.63, 22.77, 22.68, 21.54, 14.28, 14.14. Two bisiridium complexes PH-98-I (15 mg, 3%) and PH-98-III (5 mg, 2%) have also been isolated (see below).

Synthesis of PH-98-I and PH-98-III

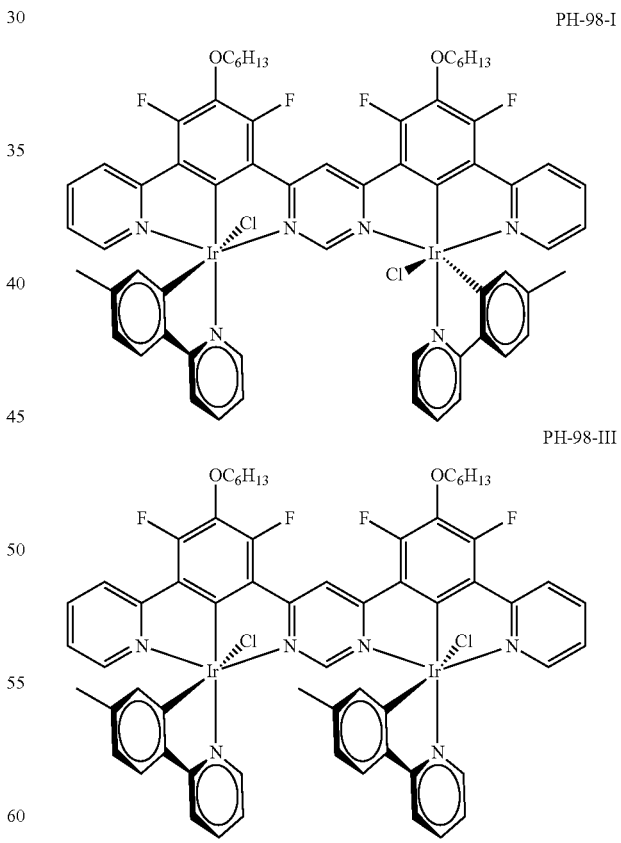

PH-98-I

PH-98-III

A mixture of PH-45 (100 mg, 0.15 mmol), $IrCl_3*nH_2O$ (117 mg, 0.32 mmol) 2-ethoxyethanol (4.5 mL) and water (1.5 mL) was heated under reflux for 12 hours. After cooling to room temperature, water was added. The formed solid was filtered off, washed with water and dried. A mixture of this solid, 2-(p-tolyl)pyridine and AgOTf (235 mg, 2.35 mmol) stirred at 115° C. for 10 h. The mixture was treated with DCM and brine. The aqueous layer was extracted with DCM (3×20 mL). The combined organic phase was dried over MgSO$_4$, filtered and DCM was removed by rotary evaporation. The excess of 2-(p-tolyl)pyridine was then distilled off in vacuum (160° C., 2 mmHg). The residue was applied to a column (silica gel DCM). The column was first eluted with pure DCM followed by a mixture of DCM/ethylacetate, 3/2). Fractions containing corresponding product were combined and evaporated to dryness. PH-98-I higher Rf value (54 mg, 25%) HRMS for [M-Cl]$^+$ Calcd 1414.3363. found 1414.3372. $^1$H NMR (CDCl$_3$, 400 MHz) δ 9.52 (d, 2H, J=5 Hz), 8.62 (s, 1H), 8.40 (d, 2H, J=8.0 Hz), 7.95 (d, 2H, J=8.0 Hz), 7.86 (ddd, 2H, J=1.4 Hz, J=7.8 Hz), 7.56 (ddd, 2H, J=1.5 Hz, J=7.8 Hz), 7.45 (d, 2H, J=8.0 Hz), 7.37 (d, 2H, J=5.0 Hz), 7.17 (m, 2H), 6.80 (ddd, 2H, J=1.5 Hz, J=6.5 Hz, J=7.4 Hz), 6.54 (d, 2H, J=7.0 Hz), 5.60 (s, 1H), 4.17 (m, 4H), 1.89 (m, 10H), 1.55 (m, 8H), 1.40 (m, 4H), 0.95 (m, 6H). $^{13}$C NMR (CDCl$_3$, 100 MHz) δ 179.18, 172.57 (d, J=7 Hz), 165.78 (d, J=7.0 Hz), 164.95, 160.37, 158.87 (dd, J=2 Hz, J=17.4 Hz), 156.17 (dd, J=2.4 Hz, J=14.2 Hz), 150.95, 148.64, 143.76, 140.50, 139.90, 137.75, 137.23, 136.62, 129.96 (dd, J=15.8 Hz), 124.49, 124.18, 123.86, 123.43, 123.31, 122.88, 121.94, 121.50 (d, J=3.9 Hz), 118.37, 114.40 (dd, J=11.9 Hz), 75.66, 31.70, 30.12, 29.78, 25.56, 22.72, 21.56, 14.17.

PH-98-III lower Rf value (42 mg 19%). PH-98-III HRMS for [M-2Cl]$^{2+}$ calcd. 689.1824. found 689.1823. $^1$H NMR (CDCl$_3$, 400 MHz) δ 9.78 (d, 2H, J=5.0 Hz), 8.63 (s, 1H), 8.04 (d, 2H, J=7.6 Hz), 7.81 (m, 4H), 7.57 (ddd, 2H, J=1.6 Hz, J=7.5 Hz), 7.33 (m, 4H), 7.22 (d, 2H, J=6.0 Hz), 7.07 (s, 1H), 6.79 (ddd, 2H, J=1.5 Hz, J=6 Hz, J=7.5 Hz), 6.41 (s, 2H, J=8.0 Hz), 4.20 (m, 4H), 1.90 (m, 4H), 1.78 (s, 6H), 1.58 (m, 8H), 1.43 (m, 8H), 0.97 (m, 6H). $^{13}$C NMR (CDCl$_3$, 100 MHz) δ 179.02, 172.47 (d, J=5.7 Hz), 165.82 (d, J=6.6 Hz), 164.25, 160.36, 158.78 (dd, J=1.9 Hz, J=21.0 Hz), 156.09 (dd, J=2.9 Hz, J=20.5 Hz), 150.96, 149.40, 144.26, 139.79, 139.62, 137.99, 137.17, 135.82, 130.06 (dd, J=15.7 Hz), 129.58, 126.86, 124.24, 123.94, 123.47, 123.31, 123.2, 122.86, 122.04, 121.48 (d, J=3.8 Hz), 118.17, 114.14 (dd, J=11.9 Hz), 75.70, 31.73, 30.18, 29.79. 25.58, 22.74, 21.35, 14.18

Example 2

PH-174

Synthesis of PH-174

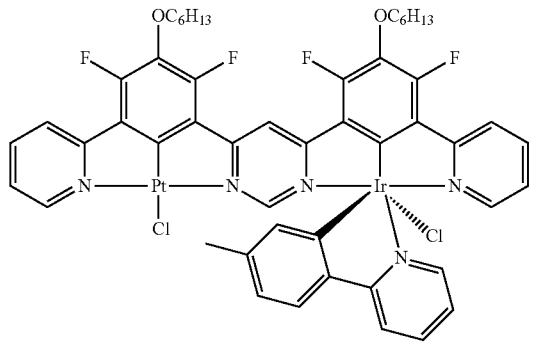

PH-174

K$_2$PtCl$_4$ (126 mg, 0.3 mmol) was added to a solution of bisterdentate ligand PH-45 (200 mg, 0.3 mmol) in acetic acid (50 mL). The reaction was heated under reflux for 10 h and the reaction was stirred at room temperature until an orange precipitate appeared. The precipitate was filtered off and no further purification was performed. The crude material was dissolved in a mixture of 2-ethoxyethanol/water (20 mL, 3/1, v/v) at 80° C. and IrCl$_3$*nH$_2$O (120 mg, 0.33 mmol) was added. The mixture was heated under reflux for 8 h. At room temperature, water (20 mL) was added and the dark solid was filtered off and washed with water (10 mL). The dark solid was air dried and was recovered in toluene (20 ml). 2-p-tolylpyridine (56 mg, 0.33 mmol) and AgOTf (338 mg, 1.32 mmol) were added to the solution and the mixture was heated under reflux for 10 h. The mixture was concentrated under vacuum and the dark solid was recovered with CH$_2$Cl$_2$ (30 mL) and washed with brine (10 mL). The organic layer was dried over MgSO4, filtered and solvent was removed by rotary evaporation. The compound was purified by semi preparative chromatography (AlO$_3$, CH$_2$Cl$_2$/EtOAc, 95/5). The compound was recovered as a dark purple powder (20 mg, 5%). $^1$H NMR (CDCl$_3$, 400 MHz) δ 10.00 (d, 1H, J=1.2 Hz), 9.07 (s, 1H), 8.68 (s, 1H), 8.34 (s, 1H), 8.14 (d, 1H, J=8.0 Hz), 8.08 (d, 1H, J=4 Hz), 7.84 (m, 2H), 7.70 (ddd, 1H, J=1.3 Hz, J=7.8 Hz), 7.62 (m, 1H), 7.52 (d, 1H, J=8.0 Hz), 7.21 (m, 1H), 6.93 (ddd, 1H, J=1.2 Hz, J=7.2 Hz), 6.59 (d, 1H, J=8.0 Hz), 5.70 (s, 1H), 4.23 (t, 2H, J=6.6 Hz), 4.09 (t, 2H, J=6.6 Hz), 1.90 (m, 4H), 1.55 (m, 4H), 1.39 (m, 8H), 0.95 (m, 6H). $^{13}$C NMR (CDCl$_3$, 100 MHz) δ 164.14, 160.67, 151.97, 151.91, 149.58, 143.51, 141.24, 139.85, 139.75, 138.72, 137.47, 136.46, 124.43, 123.80, 213.57 (dd, J=6.2 Hz), 123.37, 123.25, 119.22, 70.63, 31.72, 31.64, 30.21, 30.03, 25.60, 25.46, 22.75, 22.68, 21.46, 14.18, 14.13, 13.84.

Example 3

PH-167-I and PH-167-I

Synthesis of Bisterdentate Ligand PH-139

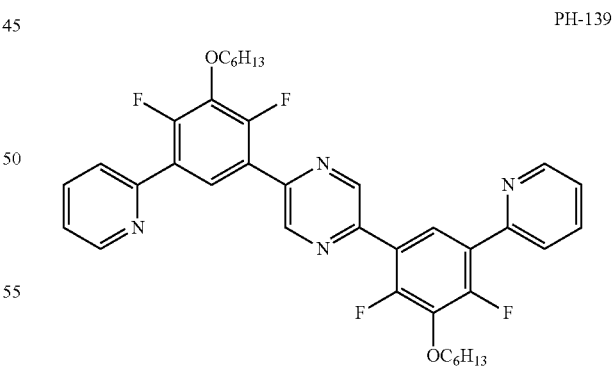

PH-139

A mixture of K$_2$CO$_3$ (3.4 g, 0.24 mmol), 2,4-difluoro-3-hexyloxy-5-(2-pyridyl)phenyl boronic acid (2.04 g, 6.1 mmol) and 2,5-dichloropyrazine (719 mg, 2.5 mmol) in a mixture of water (20 mL), toluene (40 mL) and ethanol (2 mL) was deoxygenated by bubbling N$_2$ through the mixture for 20 minutes. Pd(PPh$_3$)$_4$ (250 mg, 0.24 mmol) was then added and the mixture was heated under refluxed for 15 hours. Brine (40 mL) was added and the phases were separated. The aqueous layer was extracted with ethyl acetate (3×20 mL). The combined organic layers were dried over MgSO₄, filtered and evaporated to dryness. The product was purified by column chromatography (SiO₂, Petroleum ether/EtOAc, from 9/1 to 6/4). Colourless solid (630 mg, 38%). $^1$H NMR (400 MHz, CDCl₃) δ 9.15 (d, 1H, J=2.0 Hz), 8.74 (ddd, 2H, J=1.2 Hz, J=5.2 Hz, J=6.4 Hz), 8.39 (dd, 2H, J=8.4 Hz), 7.78 (m, 4H), 4.23 (t, 4H, J=6 Hz), 1.83 (q, 4H, J=7.2 Hz), 1.34 (m, 4H), 1.36 (m, 8H), 0.90 (t, 6H, J=7.2 Hz). $^{13}$C NMR (100 MHz, CDCl₃) δ 152.40, 150.05, 146.85, 144.58, 144.46, 136.63, 125.49, 125.31, 124.40, 124.32, 122.86, 121.34 (m), 75.57, 31.32, 30.10, 25.46, 22.68, 14.13.

Synthesis of PH-167-1 and PH-167-III

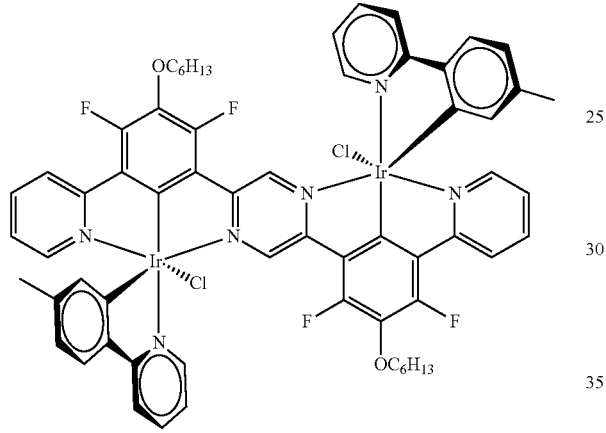

PH-167-III

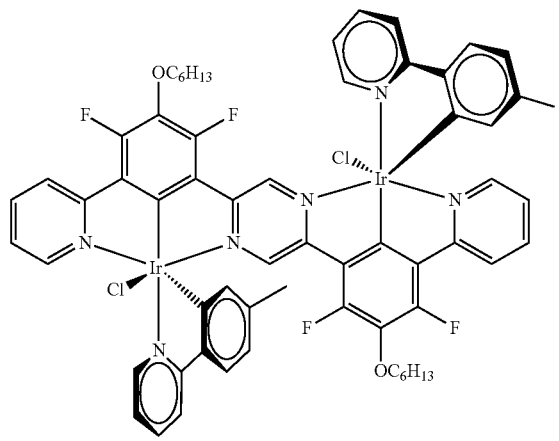

PH-167-I

A mixture of PH-139 (200 mg, 0.30 mmol), IrCl₃*nH₂O (109 mg, 0.30 mmol) 2-ethoxyethanol (25 mL) and water (9 mL) was heated under reflux for 12 hours. After cooling to room temperature, water was added. The formed solid was filtered off, washed with water and dried. The crude material was put in suspension in toluene (20 mL) and 2-(p-tolyl) pyridine (56 mg, 0.33 mmol) and AgOTf (314 mg, 1.2 mmol) stirred at 115° C. for 10 h under inert atmosphere. At room temperature, brine was added to the mixture, the organic layer was collected and the aqueous layer extracted with DCM (3×10 mL). The combined organic layers were dried over MgSO₄ and the solvent remove by rotary evaporation. The crude material was purified using aluminium oxide preparative chromatography using CHCl₃/ethyl acetate (7/3, v/v) as eluent to give PH-167-I and PH-167-III. PH-167-III: $^1$H NMR (400 MHz, CDCl₃) δ 10.07 (d, 2H, J=2.8 Hz), 8.12 (s, 2H), 8.09 (s, 2H), 8.47 (m, 6H), 7.61 (m, 6H), 7.49 (d, 2H, J=7.6 Hz), 6.85 (ddd, 2H, J=2.1 Hz, J=5.9 Hz, J=7.0 Hz), 6.55 (dd, 2H, J=1.2 Hz, J=8.0 Hz), 5.63 (d, 2H, J=1.2 Hz), 4.09 (dt, 4H, J=1.2 Hz, J=6.5 Hz), 1.83 (m, 4H), 1.41 m, 8H), 0.98 (t, 6H, J=6.8 Hz). $^{13}$C NMR (100 MHz, CDCl₃) δ 164.58, 151.82, 149.65, 144.31, 143.34, 140.94, 139.90, 138.26, 137.51, 137.47, 129.82, 123.92, 123.69, 122.90, 122.73, 118.90, 75.65, 62.83, 31.69, 30.04, 29.78, 25.56, 22.92, 21.44. PH-167-I has very similar analytical data.

Example 4

N-170-3

Synthesis of Bisterdentate Ligand PH-144

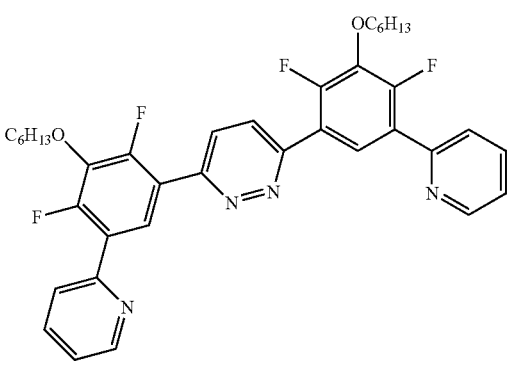

PH-144

A mixture of K₂CO₃ (3.3 g, 0.24 mmol), 2,4-difluoro-3-hexyloxy-5-(2-pyridyl)phenyl boronic acid (2.0 g, 6.0 mmol) and 2,5-dichloropyrazine (372 mg, 2.5 mmol) in a mixture of water (40 mL), toluene (20 mL) and ethanol (2 mL) was deoxygenated by bubbling N₂ through the mixture for 20 minutes. Pd(PPh₃)₄ (250 mg, 0.24 mmol) was then added and the mixture was heated under reflux for 15 hours. Brine (40 mL) was added and the phases were separated. The aqueous layer was extracted with ethyl acetate (3×20 mL). The combined organic layers were dried over MgSO₄, filtered and evaporated to dryness. The product was purified by column chromatography (SiO₂, Petroleum ether/EtOAc, from 7/3 to 5/5). Colourless solid (1.3 g, 79%). $^1$H NMR (400 MHz, CDCl₃) δ 9.15 (d, 1H, J=2.0 Hz), 8.71 (ddd, 2H, J=1.4 Hz, J=4.9 Hz, J=6.2 Hz), 8.51 (dd, 2H, J=8.4 Hz), 8.01 (s, 2H), 7.77 (m, 4H), 7.28 (ddd, 2H, J=1.9 Hz, J=4.8 Hz, J=6.6 Hz), 4.23 (t, 4H, J=6.8 Hz), 1.83 (q, 4H, J=7.1 Hz), 1.51 (m, 4H), 1.34 (m, 8H), 0.90 (t, 6H, J=7.0 Hz). $^{13}$C NMR (100 MHz, CDCl₃) δ 156.69 (d, J=5.7 Hz), 156.20 (d, J=4.7 Hz), 154.21, 154.12, 153.67 (d, J=4.7 Hz), 152.53, 149.96, 136.61, 127.07 (d, J=8.6 Hz), 125.60, 125.44 (dd, J=3.8 Hz, J=11.4 Hz), 124.30 (d, J=7.6), 122.85, 121.44 (dd, J=3.3 Hz, J=10.0 Hz), 75.57, 31.62, 30.09, 25.45, 22.68, 14.13.

Synthesis of N-170-3

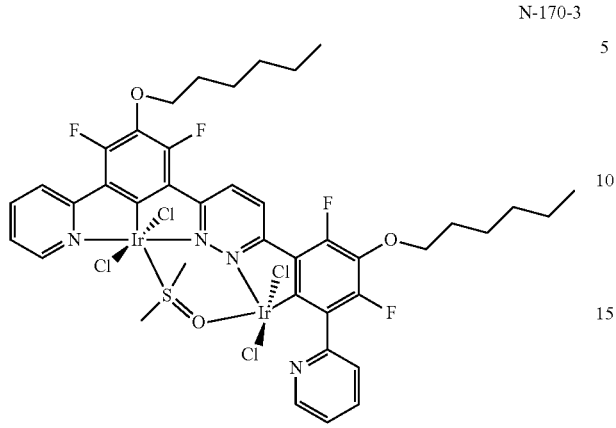

The ligand PH 144 (1 eq, 205 mg, 0.31 mmol) was dissolved in ethoxyethanol (12 cm³) with stirring and heating. Water (4 cm³) and iridium chloride hydrate (226 mg, 0.62 mmol) were added and the mixture was heated under reflux for 30 min and then stirred at 90° C. for 16 hours. The solvent was evaporated to dryness and the residue was treated with 5 ml of methanol. The solid formed was filtered, washed with methanol to give red solid. This solid was put in a test tube, DMSO (2 ml) was added and the mixture was heated at 170° C. for 5 minutes. Water was added and the mixture was extracted with chloroform. Organic layer was separated, washed with brine and dried over MgSO₄. The solvent was removed by rotary evaporation. The residue was treated with methanol. The solid was filtered off washed with methanol to give N-170-3. Yield 110 mg.

Example 5

PH-214-II

Synthesis of 2,3,4-trifluoro-3-hexyloxyphenyl boronic acid (PH-161)

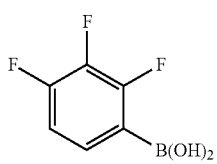

To a stirred solution of 2,3,4-trifluoro-3-hexyloxybenzene (10 g, 75.7 mmol) in dry THF (100 mL), at −78° C., n-butyllithium (1.6 M solution in hexane, 48 mL, 75.7 mmol) was added slowly. Solution was stirred at −78° C. for 2 hours. Triisopropylborate (35 mL, 151.4 mmol) was added slowly and the mixture was stirred over night. During this time the temperature slowly reached room temperature. The mixture was acidified by addition of 4M aqueous hydrochloric acid. Brine (30 mL) was added, layers separated and the aqueous layer was extracted with ethyl acetate. Combined organic layers were dried over MgSO₄ and all volatile components were removed by rotary evaporation under reduced pressure. The product was then washed with petroleum ether (20 mL) and the bright white solid was filtered out (8.6 g, 65%). NMR spectra are not well resolved.

Synthesis of PH-184

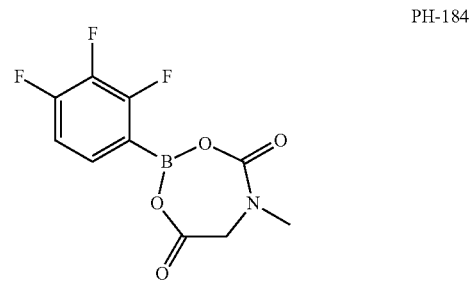 [SMILES: CN1CC(=O)OB(c2ccc(F)c(F)c2F)OC1=O]

N-Methyliminodiacetic acid (1.57 g, 9.4 mmol) was added to a solution of PH-161 (1.50 g, 8.53 mmol) in DMSO (15 mL) and Toluene (35 mL). The solution was then heated under reflux for 3 h. At room temperature, water was added and the white precipitate was filtered off, washed with water and air dried. The product was obtained as a white powder (4.28 g, 87%). No further purification was carried out.

Synthesis of PH-179

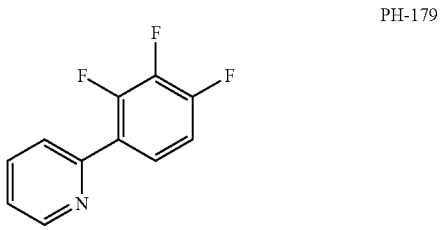 [SMILES: Fc1ccc(-c2ccccn2)c(F)c1F]

2-bromopyridine (1.38 g, 8.71 mmol) was added to a solution of PH-184 (3 g, 10.45 mmol) in 1,4-dioxane (100 mL) and the mixture was degassed for 20 min by bubbling N₂. A degassed aqueous solution of K₃PO₄ (22 mL, 3 M) was added, the mixture was then degassed during 5 min, Pd(PPH₃)₄ (508 mg, 0.34 mmol) was added and the mixture was heated at 110° C. for 15 h. At room temperature, layers were separated and the aqueous layer was extracted with ethyl acetate (3×10 mL). The combined organic layers were washed with brine, dried over MgSO₄ and all volatile compounds were removed under vacuum. A chromatography column (SiO₂, Petroleum ether/Ethyl acetate, 7/3) gave the desired compounds (1.4 g, 64%).

Synthesis of PH-196

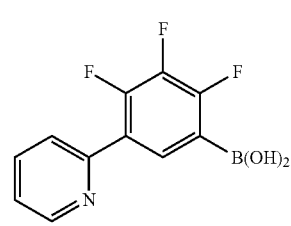

n-Butyllithium (1.6 M solution in hexane, 4.7 mL, 7.44 mmol) was added slowly with stirring to a solution of PH-179 (1.3 g, 6.2 mmol) and N,N,N'N',N-pentamethyldiethylenetriamine (1.6 mL, 7.44 mmol) in dry THF (40 mL)

at −78° C. Solution was stirred at −78° C. for 2 hours. Triisopropylborate (2.9 mL, 12.4 mmol) was added slowly and the mixture was allowed to warm to room temperature over a period of 14 hours. The mixture was neutralised by addition of diluted acetic acid. Brine (15 mL) was added, layers separated and the aqueous layer was extracted with ethyl acetate (3×15 mL). Combined organic layers were dried over $MgSO_4$, filtered and all volatiles were removed under reduced pressure. The crude product was used in the next step without further purification.

Synthesis of PH-197

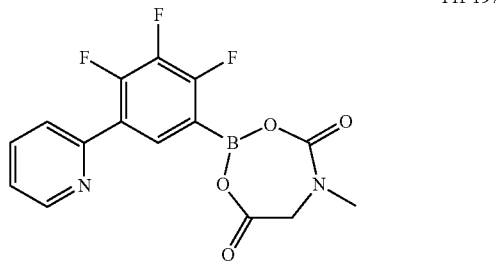

PH-197

N-Methyliminodiacetic acid (1.02 g, 6.1 mmol) was added to a solution of PH-196 (1.40 g, 5.53 mmol) in DMSO (11 mL) and Toluene (24 mL). The solution was then heated under reflux for 3 h. At room temperature, water was added and the white precipitate was filtered off, washed with water and air dried. The product was obtained as a white powder (2.045 g, quantitative). No further purification was carried out. $^1$H NMR (400 MHz, DMSO-$d_6$) δ 8.71 (d, 1H, J=4.0 Hz), 7.93 (ddd, 1H, J=1.6 Hz, J=7.5 Hz), 7.83 (ddd, 1H, J=2.2 Hz, J=6.8 Hz, J=8.6 Hz), 7.78 (d, 1H, J=7.6 Hz), 7.42 (m, 1H), 4.40 (d, 2H, J=17.6 Hz) 4.12 (17.6 Hz), 2.67 (s, 3H). $^{13}$C NMR (100 MHz, DMSO-$d_6$) δ 169.43, 155.00 (d, J=7.7 Hz), 125.53 (d, J=6.7 Hz), 151.44, 151.20 (d, J=10.5 Hz), 150.47, 148.67 (d, J=10.5 Hz), 137.69, 129.80 (d, J=8.6 Hz), 124.78 (dd, J=3.4 Hz, 8.1 Hz), 124.59 (d, J=7.6 Hz), 1213.94, 62.97, 48.21.

Synthesis of PH-200

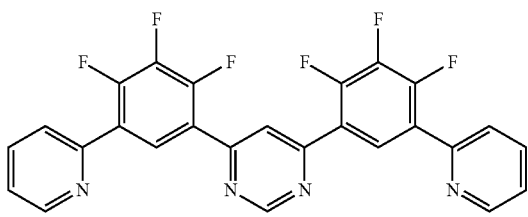

PH-200

2-4-dichloropyrimidine (178 mg, 1.2 mmol) was added to a solution of PH-197 (1.0 g, 2.8 mmol) in 1,4-dioxane (14 mL) and the mixture was degassed for 20 min by bubbling $N_2$. A degassed aqueous solution of $K_3PO_4$ (3 mL, 3 M) was added, the mixture was then degassed for an additional 5 min, Pd(PPH$_3$)$_4$ (161 mg, 0.14 mmol) was added and the mixture was heated at 110° C. for 15 h. At room temperature, brine (20 mL) was added, layers were separated and the aqueous layer was extracted with ethyl acetate (3×10 mL). The combined organic layers were dried over $MgSO_4$ and all volatile compounds were removed under vacuum. A chromatography column ($SiO_2$, Petroleum ether/Ethyl acetate, from 8/2 to 5/5) gave the desired compounds (60 mg, 10%). $^1$H NMR (400 MHz, CDCl$_3$) δ 9.41 (d, 1H, J=1.2 Hz), 8.77 (ddd, 2H, J=1.4 Hz, J=4.7 Hz), 8.67 (ddd, 2H, J=2.7 Hz, J=8.3 Hz), 8.31 (d, 1H, J=1.2 Hz), 7.81 (m, 4H), 7.33 (m, 2H).

Synthesis of PH-214-II and PH-214-I

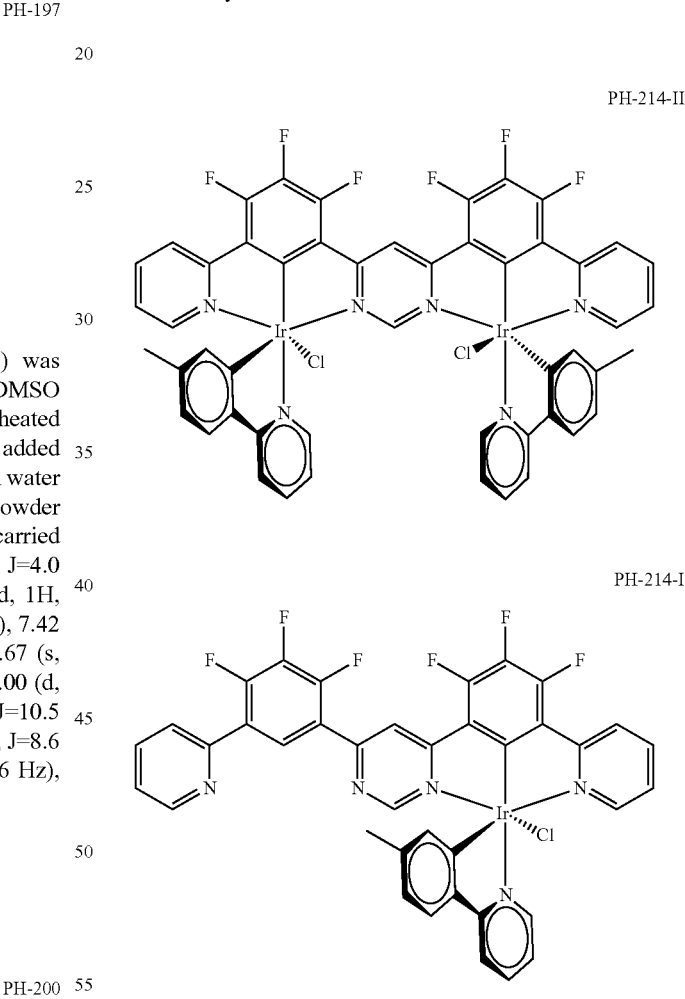

A mixture of PH-200 (40 mg, 0.08 mmol), IrCl$_3$*nH$_2$O (54 mg, 0.18 mmol) 2-ethoxyethanol (6.5 mL) and water (2 mL) was heated under reflux for 12 hours. After cooling to room temperature, water was added. The formed solid was filtered off, washed with water and dried. The crude material was put in suspension in toluene (15 mL) and 2-(p-tolyl)pyridine (29 mg, 0.17 mmol) and AgOTf (123 mg, 0.48 mmol) stirred at 115° C. for 10 h under inert atmosphere. At room temperature, brine was added to the mixture, the organic layer was collected and the aqueous layer extracted with DCM (3×10 mL). The combined organic layers were dried over MgSO$_4$ and the solvent removed by rotary evaporation. The crude material was purified using aluminium oxide preparative chromatography using CHCl$_3$/ethyl acetate (7/3, v/v) as eluent. Two products were isolated:

PH-214-I: $^1$H NMR (400 MHz, CDCl$_3$) δ 10.05 (d, 1H, J=5.6 Hz), 8.68 (d, 1H, J=4.8 Hz), 8.52 (ddd, 1H, J=2.0 Hz, J=8.2 Hz), 8.49 (s, 1H), 8.28 (d, 1H, J=0.8 Hz), 8.14 (d, 1H, J=8.0 Hz), 8.05 (d, 1H, J=8.0 Hz), 7.98 (ddd, 1H, J=1.9 Hz, J=7.8 Hz), 7.76 (m, 2H), 7.68 (m, 2H), 7.52 (m, 2H), 7.27 (ddd, 1H, J=1.7 Hz, J=4.7 Hz, J=6.6 Hz), 6.93 (ddd, 1H, J=1.4 Hz, J=6.0 Hz, J=7.4 Hz), 6.61 (dd, 1H, J=1.0 Hz, J=8.2 Hz), 5.75 (s, 1H), 1.96 (s, 3H).

PH-214-II: $^1$H NMR (400 MHz, CDCl$_3$) δ 9.51 (d, 2H, J=5.6 Hz), 8.62 (s, 1H), 8.06 (d, 2H, J=8.0 Hz), 7.96 (d, 2H, J=8.0 Hz), 7.88 (ddd, 2H, J=1.3 Hz, J=5.7 Hz), 7.61 (ddd, 2H, J=1.5 Hz, 7.8 Hz), 7.46 (d, 2H, J=7.2 Hz), 7.38 (d, 2H, J=5.6 Hz), 7.19 (3H, m), 6.83 (ddd, 2H, J=1.4 Hz, J=6.4 Hz, J=7.4 Hz), 6.57 (d, 2H, J=8.0 Hz), 5.59 (s. 2H), 1.93 (s, 6H).

Photophysical Properties

The luminescent and photophysical properties of the following mono-iridium complex and di-iridium complexes from example 1 were investigated:

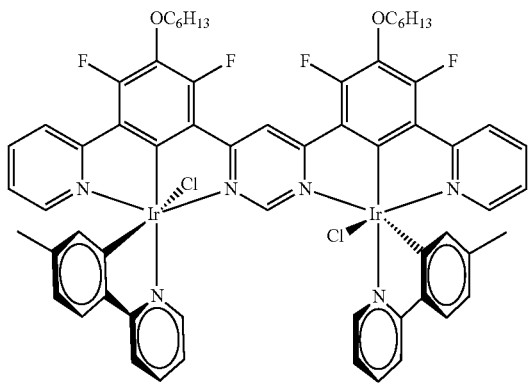

PH-98-I

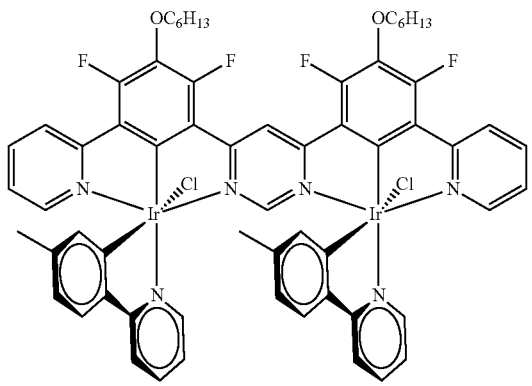

PH-98-III

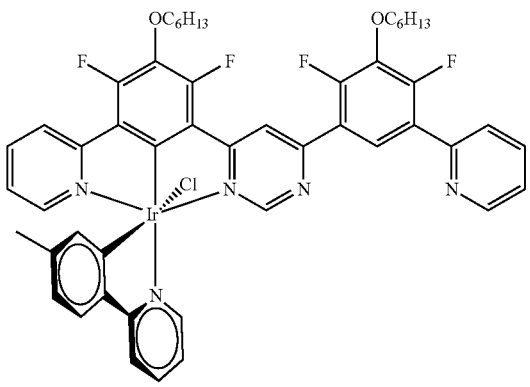

PH-98-II

Figure 2:
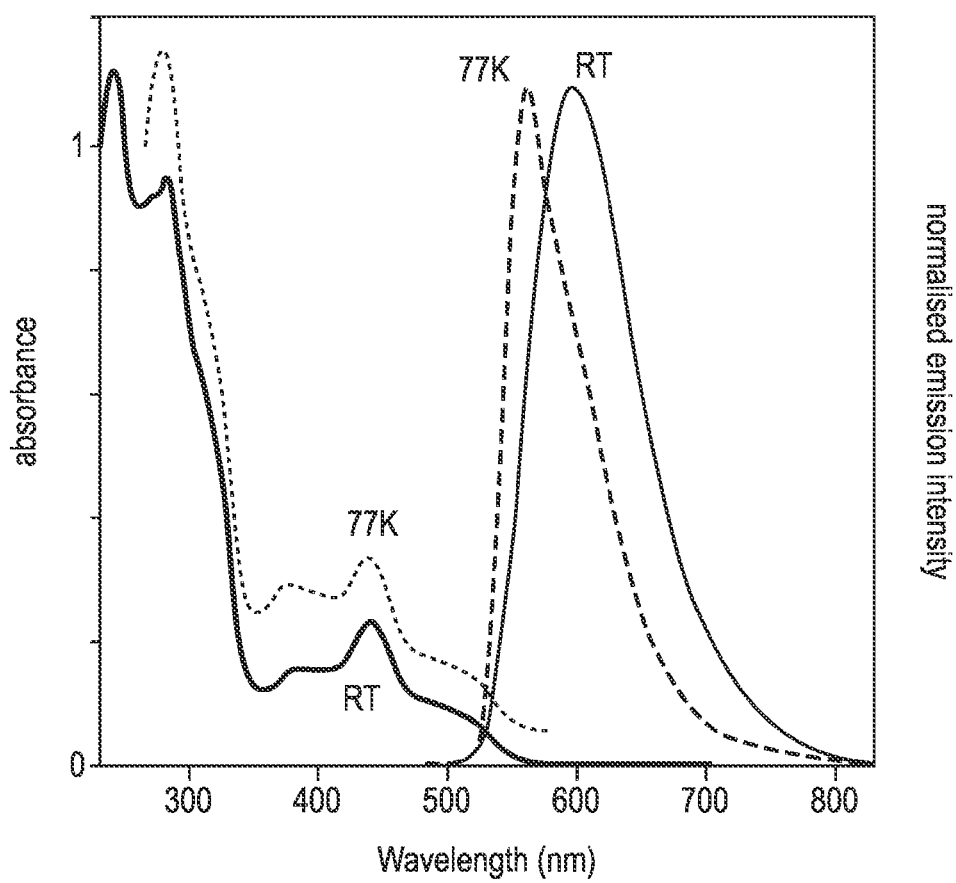
FIG. 2 shows absorption and emission spectra for the monoiridium complex PH-98-II recorded at room temperature (RT) and at 77K.
Figure 3:
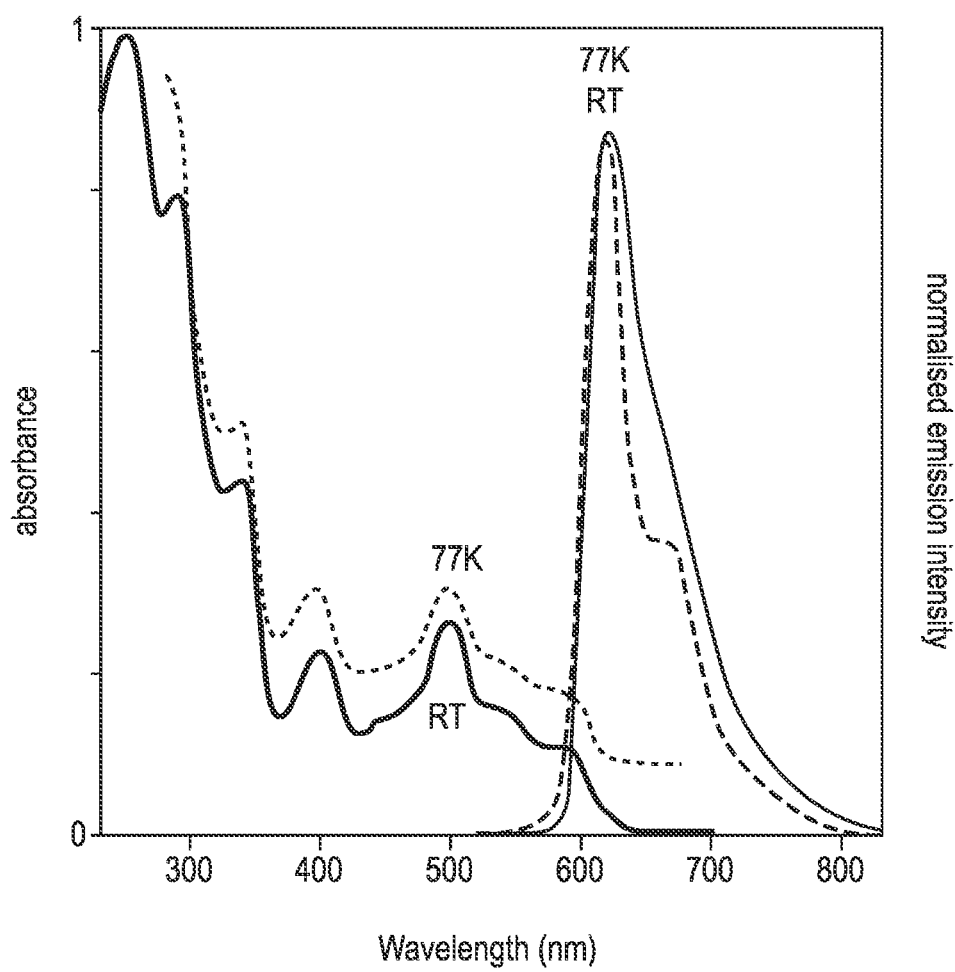
FIG. 3 shows absorption and emission spectra for the di-ridium complex PH-98-I recorded at room temperature (RT) and at 77K.

Absorption and emission spectra for the di-iridium complexes PH-98-I and PH-98-III and for the monoiridium complex, PH-98-II, recorded at room temperature and at 77K are shown in FIGS. 1, 2 and 3. The photophysical properties of di-iridium complexes PH-98-I and PH-98-III were measured and compared to the monoiridium complex PH-98-II. The results showing emission data for each complex are displayed in Table 1:

TABLE 1

Emission data for Iridium complexes PH-98-I, PH-98-II and PH-98-III
Emission data in degassed CH$_2$Cl$_2$ at 298K

| Complex | $\lambda_{max}$/nm | $\Phi_{lum}$ [a] | τ/ns [b] | $k_r$ [c]/ $10^5$ s$^{-1}$ | $\Sigma k_{nr}$ [c]/ $10^5$ s$^{-1}$ | $k_Q^{O2}$ [d]/ $10^8$ M$^{-1}$s$^{-1}$ | Emission at 77K [e] $\lambda_{max}$/nm | τ/ns |
|---|---|---|---|---|---|---|---|---|
| PH98-2 | 595 | 0.59 | 2800 [450] | 2.1 | 1.5 | 8.5 | 562 | 13000 |
| PH98-1 | 622 | 0.65 | 760 [520] | 8.6 | 4.6 | 2.8 | 617, 666 | 3700 |
| PH98-3 | 625 | 0.65 | 730 [460] | 8.9 | 4.8 | 3.7 | 620, 672 | 3500 |

(a) Measured using [Ru(bpy)$_3$]Cl$_2$ as the standard.

(b) Values in air-equilibrated solution in parenthesis.

(c) $k_r$ and $\Sigma k_{nr}$ are the radiative and non-radiative decay rate constants, estimated from the quantum yield and lifetime assuming that the emissive state is formed with unitary efficiency.

(d) Biomolecular rate constant for quenching by O$_2$, estimated from the luminescence lifetimes in degassed air-equilibrated solutions, and taking [O = 2.2 mM in CH$_2$Cl$_2$ at p = 1 atm air and T = 298K.

(e) In diethyl ether/isopentane/ethanol (2:2:1 v/v)

As demonstrated by the values in Table 1 and as depicted in FIG. 1, considerable changes in the properties are induced by the addition of a second metal centre whereas little difference is observed between PH-98-I and PH-98-III which differ only by stereochemical configuration. The data in Table 1 shows that the addition of the second metal centre causes a 27 nm and a 30 nm red-shift in emission for the complexes PH-98-I and PH-98-III respectively. Despite the red-shift, luminescent quantum yields remained high (65% for both PH-98-I and PH-98-III). In fact, the luminescent quantum yield for the di-iridium complexes (65%) is greater than for the monoiridium complex PH-98-II (59%). This is despite the band gap law which implies that red-shift would ordinarily result in a decrease in quantum yield. Such luminescent quantum yields and quantum efficiency achieved by the compounds of the present invention are comparable with the best known red-emitters. It should also be pointed out that the Stokes shift in bimetallic compounds, equating to the difference between positions of the band maxima of the absorption and emission spectra, is very small and this is in accordance with the experimental data. Furthermore, the emission spectra for PH-98-I as shown in FIG. 3 changes very little when cooling from room temperature to 77 K (the absorption and emission spectra for PH-98-III recorded at 77K and room temperature are not shown but were very similar to that of PH-98-I). This is in contrast to the emission spectra for the monoirdidum complex PH-98-II as shown in FIG. 2, wherein a considerable shift in the emission spectra is noted when cooling from room temperature to 77 K. This data indicates that the system is very rigid for the bimetallic compounds PH-98-I and PH-98-III, which is a favourable factor in achieving high quantum yields.

Table 1 also shows that the introduction of the second metal centre for the complexes PH-98-I and PH-98-III results in a decrease of the emission life time (τ) at 298K compared to the monometallic complex PH-98-II (760 and 730 ns for PH-98-I and PH-98-III respectively versus 2800 ns for PH-98-II). Characteristics such as those exhibited by PH-98-I and PH-98-III are particularly suited to OLEDs where a short emission life time is preferable. Compounds that demonstrate short emission life times minimise the probability of triplet-triplet annihilation whereas compounds with a longer lifetime of emission, such as those with only a single metal centre, are more likely to undergo decay without the emission of light.

The compounds of the present invention may be incorporated into OLED devices using techniques familiar to those skilled in the art. Thus the present invention also includes OLEDs and other such devices comprising the compounds described herein.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A cyclometallated organometallic light emitting complex having a first tridentate ligand portion coordinated with a first metal and a second tridentate ligand portion coordinated with a second metal, the complex having a structure according to Formula (IV):

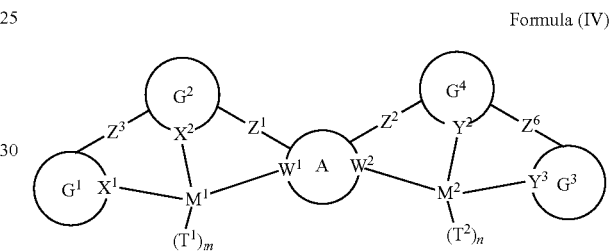

Formula (IV)

wherein:
A is selected from the group consisting of pyrimidine, and wherein $W^1$ and $W^2$ are the nitrogen atoms of said pyrimidine ring;
wherein $M^1$ and $M^2$ are each iridium;
wherein $G^1$ and $G^2$ represent first and second aromatic moieties respectively and $Z^3$ is one or more bonds by which the first aromatic moiety $G^1$ is joined to the second aromatic moiety $G^2$ and
wherein $G^3$ and $G^4$ represent first and second aromatic moieties respectively and $Z^6$ is one or more bonds by which the first aromatic moiety $G^3$ is joined to the second aromatic moiety $G^4$;
wherein $X^1$, $X^2$ and $W^1$ are coordinated to metal atom $M^1$;
wherein $Y^1$, $Y^2$ and $W^2$ are coordinated to metal atom $M^2$;
wherein at least one of atoms $X^1$ and $X^2$ is connected to said metal atom $M^1$ via an organometallic bond and/or wherein at least one of atoms $Y^1$ and $Y^2$ is connected to said metal atom $M^2$ via an organometallic bond;
wherein each of $X^1$, $X^2$, $Y^1$ and $Y^2$ is independently carbon or nitrogen;
$Z^1$ and $Z^2$ are one or more bonds;
$T^1$ and $T^2$ are auxiliary ligands in which m and n are 0 or an integer sufficient to satisfy the respective coordination requirements of $M^1$ and $M^2$, and where m and n are 2 or more, each respective auxiliary ligand may be the same or different.

2. The complex according to claim 1, wherein at least one of $X^1$, $X^2$, $Y^1$ and $Y^2$ is carbon.

3. The complex according to claim 1, wherein at least one of $X^1$ and $X^2$ is carbon and at least one of $Y^1$ and $Y^2$ is carbon.

4. The complex according to claim 1, wherein each of $Y^1$ and $Y^2$ is independently carbon or nitrogen.

5. The complex according to claim 1, wherein one of $Y^1$ and $Y^2$ is nitrogen and the other is carbon.

6. The complex according to claim 1, having the structure of general Formula (X):

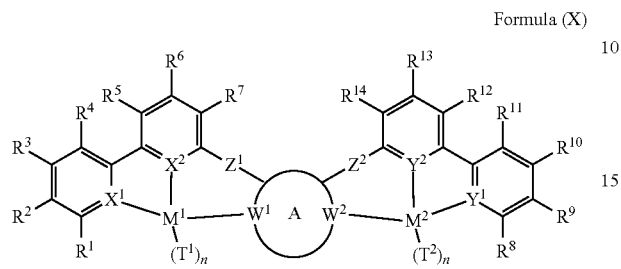

Formula (X)

wherein $R^1$ to $R^{14}$ are each independently selected from the group consisting of H and a substituent.

7. An organic light emitting diode (OLED) comprising or including a complex as claimed in claim 1.

* * * * *